US007534937B2

(12) United States Patent
Hammer et al.

(10) Patent No.: US 7,534,937 B2
(45) Date of Patent: May 19, 2009

(54) GENES CONFERRING HERBICIDE RESISTANCE

(75) Inventors: Philip E. Hammer, Cary, NC (US); Todd K. Hinson, Rougemont, NC (US)

(73) Assignee: Athenix Corporation, Research Triangle Park, NC (US)

( * ) Notice: Subject to any disclaimer, the term of this patent is extended or adjusted under 35 U.S.C. 154(b) by 271 days.

(21) Appl. No.: 11/315,678

(22) Filed: Dec. 22, 2005

(65) Prior Publication Data

US 2006/0150270 A1 Jul. 6, 2006

Related U.S. Application Data

(60) Provisional application No. 60/640,195, filed on Dec. 29, 2004.

(51) Int. Cl.
C12N 15/82 (2006.01)
C12N 15/52 (2006.01)
C12N 15/63 (2006.01)

(52) U.S. Cl. .................. 800/300; 435/252.3; 435/320.1; 435/419; 536/23.2; 800/288; 800/298

(58) Field of Classification Search ....................... None
See application file for complete search history.

(56) References Cited

U.S. PATENT DOCUMENTS

| | | | |
|---|---|---|---|
| 4,769,061 A | 9/1988 | Comai et al. | |
| 4,940,835 A | 7/1990 | Shah et al. | |
| 4,971,908 A | 11/1990 | Kishore et al. | |
| 5,118,642 A | 6/1992 | Yoshino et al. | |
| 5,145,783 A | 9/1992 | Kishore et al. | |
| 5,310,667 A | 5/1994 | Eichholtz et al. | |
| 5,312,901 A | 5/1994 | Fahnestock | |
| 5,627,061 A | 5/1997 | Barry et al. | |
| 5,633,435 A * | 5/1997 | Barry et al. ................. | 800/288 |
| 5,776,760 A | 7/1998 | Barry et al. | |
| 5,804,425 A | 9/1998 | Barry et al. | |
| 5,886,775 A | 3/1999 | Houser et al. | |
| 6,225,114 B1 | 5/2001 | Eichholtz et al. | |
| 6,248,876 B1 | 6/2001 | Barry et al. | |
| 6,492,578 B1 * | 12/2002 | Staub et al. ................. | 800/300 |
| 2002/0007053 A1 | 1/2002 | Barry et al. | |
| 2003/0233675 A1 | 12/2003 | Yongwei et al. | |
| 2005/0223436 A1 | 10/2005 | Lin et al. | |

FOREIGN PATENT DOCUMENTS

WO WO 96/16174 * 5/1996
WO WO 2005/014820 A 2/2005

OTHER PUBLICATIONS

Barry, G., et al., "Inhibitors of Amino Acid Biosynthesis: Strategies for Imparting Glyphosate Tolerance to Crop Plants," *Current Topics in Plant Physiology*, American Society of Plant Psysiologists, Rockville, MD, 1992, pp. 139-145.

Fitzgibbon, J.E., and H.D. Braymer, "Cloning of a Gene from *Pseudomonas* sp. Strain PG 2982 Conferring Increased Glyphosate Resistance," *Applied and Environmental Microbiology*, Nov. 1990, pp. 3382-3388, vol. 56, No. 11.

He, M., et al., "A New Type of Class I bacterial 5-Enopyruvylshikimate-3-phosphate Synthase Mutants with Enhanced Tolerance to Glyphosate," *Biochemica et Biophysica Acta*, Nov. 7, 2001, pp. 1-6; vol. 1568, No. 1.

Saroha, M.K., et al., "Glyphosate-Tolerant Crops: Genes and Enzymes," *J. Plant Biochemistry & Biotechnology*, Jul. 1998, pp. 65-72, vol. 7.

Schultz, A., et al., "Differential Sensitivity of Bacterial 5-Enolpyruvylshikimate-3-phosphate Synthases to the Herbicide Glyphosate," *FEMS Microbiology Letters*, 1985, pp. 297-301, vol. 28, No. 3.

Sost, D., and Nikolaus Amrhein, "Substitution of Gly-96 to Ala in the 5-Enolpyruvylshikimate 3-Phosphate Synthase of *Klebsiella pneumoniae* Results in a Greatly Reduced Affinity to the Herbicide Glyphosate," *Archives of Biochemistry and Biophysics*, Nov. 1, 1990, pp. 433-436, vol. 282, No. 2.

Wood, E.W., et al., "The Genome of the Natural Genetic Engineer *Agrobacterium tumefaciens* C58," *Science*, Dec. 14, 2001, pp. 2317-2323, vol. 294.

EMBL Database Accession No. AE009032, Submitted Sep. 27, 2001.

* cited by examiner

Primary Examiner—David H Kruse
(74) Attorney, Agent, or Firm—Alston & Bird LLP

(57) ABSTRACT

Compositions and methods for conferring herbicide resistance to bacteria, plants, plant cells, tissues and seeds are provided. Compositions comprising a coding sequence for a polypeptide that confers resistance or tolerance to glyphosate herbicides are provided. The coding sequences can be used in DNA constructs or expression cassettes for transformation and expression in plants. Compositions also comprise transformed bacteria, plants, plant cells, tissues, and seeds. In particular, isolated nucleic acid molecules corresponding to glyphosate resistant nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:3 or the nucleotide sequence set forth in SEQ ID NO:1 or 2.

15 Claims, 2 Drawing Sheets

FIG. 1

```
              *         320         *         340         *         360         *         380         *         400
grgB      : AVLAAFNEMPVRFVGIENLRVKECDRIRALSSGLSRIVPNLGTEEGDDLIIASDPSLAGKILTAEIDSFADHRLAMSFALAGLKIGGITILDPDCVAKTFP :  404
grg8m1_(C22) : .................................................................................................. :  404
grg8m3_(N24) : .................................................................................................. :  404
grg8m2_(N15) : .................................................................................................. :  404
grg8m4_(A1)  : .................................................................................................. :  404
grg8m5_(B2)  : .................................................................................................. :  404
grg8m6_(B7)  : ...........................................S...................................................... :  404
grg8m7_(B11) : ..........................A....................N.................................................. :  404
grg8m8_(C11) : ..............................N................................................................... :  404
grg8m9_(E3)  : ...............................................................................V.................. :  404
grg8m10_(F4) : .................................................................................................. :  404

*         420
grgB      : SYWNVLSSLGVAYED- :  419
grg8m1_(C22) : ...............- :  419
grg8m3_(N24) : ...............- :  419
grg8m2_(N15) : ...............- :  419
grg8m4_(A1)  : ...............- :  419
grg8m5_(B2)  : ...............- :  419
grg8m6_(B7)  : ...............- :  419
grg8m7_(B11) : ...............- :  419
grg8m8_(C11) : ...............- :  419
grg8m9_(E3)  : ...............- :  419
grg8m10_(F4) : ...............- :  419
```

FIG. 1 (continued)

SEQUENCE LISTING

<160> NUMBER OF SEQ ID NOS: 23

<210> SEQ ID NO 1
<211> LENGTH: 2000
<212> TYPE: DNA
<213> ORGANISM: Brevundomonas vesicularis
<220> FEATURE:
<221> NAME/KEY: CDS
<222> LOCATION: (296)...(1555)

<400> SEQUENCE: 1

```
ggtttcgtcg aattgcagca gtcgctggag cggaccgaaa acgaaatcca gatgtcgcgc    60
cgctattaca acggtgccgc acgcgatctg aacgtcaagg tcgagacctt cccgaacaat   120
ctcattgccg gccccttcgg cttcgtcaag aaggcctatt tcgagatcac caacgaggcc   180
gatcgcgccg ttcccacggt caagttctaa gattttcgct atcggttttt catgcaaggc   240
ggtaaaggat ggccgaccgc cggccatcgg ccgttttcct gactgaccaa agaga atg   298
                                                                Met
                                                                 1
```

| | | | | | | | | | | | | | | | |
|---|---|---|---|---|---|---|---|---|---|---|---|---|---|---|---|
| atg | atg | ggt | aga | gcc | aaa | ctc | acg | att | atc | ccg | ccg | ggc | aag | cct | ttg |
| Met | Met | Gly | Arg | Ala | Lys | Leu | Thr | Ile | Ile | Pro | Pro | Gly | Lys | Pro | Leu |
|     |     |     | 5   |     |     |     | 10  |     |     |     |     | 15  |     |     |     |

346

```
acc gga cgc gcc atg ccg ccg gga tcg aag tcg atc acc aac cgc gca   394
Thr Gly Arg Ala Met Pro Pro Gly Ser Lys Ser Ile Thr Asn Arg Ala
             20                  25                  30 ttg ctg ctc gcc ggc ctc gcc aag ggc acg agc cgg cta acc ggt gcg   442
Leu Leu Leu Ala Gly Leu Ala Lys Gly Thr Ser Arg Leu Thr Gly Ala
 35                  40                  45 ctg aag agc gac gat acc cgc tat atg gcc gaa gcg ctg cgt gcg atg   490
Leu Lys Ser Asp Asp Thr Arg Tyr Met Ala Glu Ala Leu Arg Ala Met
 50                  55                  60                  65 ggt gta acg atc gac gag ccc gac gac acc acg ttc atc gtc aaa ggc   538
Gly Val Thr Ile Asp Glu Pro Asp Asp Thr Thr Phe Ile Val Lys Gly
                 70                  75                  80 agc ggc aag ctg cag ccg ccg gca gcc ccg ctt ttc ctc ggc aat gcc   586
Ser Gly Lys Leu Gln Pro Pro Ala Ala Pro Leu Phe Leu Gly Asn Ala
             85                  90                  95 ggc acg gca acg cgc ttc ctg acg gcg gcc gcg gca ctg gtg gac ggc   634
Gly Thr Ala Thr Arg Phe Leu Thr Ala Ala Ala Ala Leu Val Asp Gly
            100                 105                 110 aag gtc atc gtc gac ggc gat gcc cat atg cgc aag cgg ccg atc gga   682
Lys Val Ile Val Asp Gly Asp Ala His Met Arg Lys Arg Pro Ile Gly
115                 120                 125 ccg cta gtc gac gcg ttg cgc tcg ctc ggc atc gat gcc tcg gct gaa   730
Pro Leu Val Asp Ala Leu Arg Ser Leu Gly Ile Asp Ala Ser Ala Glu
130                 135                 140                 145 acc ggc tgc ccg cca gtc acg atc aac ggc acc ggc cgc ttc gag gca   778
Thr Gly Cys Pro Pro Val Thr Ile Asn Gly Thr Gly Arg Phe Glu Ala
                150                 155                 160 agc cgc gtg cag atc gat ggc ggc ctg tcc agc cag tat gtc tcg gcg   826
Ser Arg Val Gln Ile Asp Gly Gly Leu Ser Ser Gln Tyr Val Ser Ala
            165                 170                 175 ctc ctg atg atg gcc gcc ggc ggc gat cgc gct gtc gat gtc gag ctt   874
Leu Leu Met Met Ala Ala Gly Gly Asp Arg Ala Val Asp Val Glu Leu
        180                 185                 190 ctc ggc gaa cat atc ggc gct ctc ggc tat atc gac ctg acc gtt gcc   922
Leu Gly Glu His Ile Gly Ala Leu Gly Tyr Ile Asp Leu Thr Val Ala
    195                 200                 205
```

```
gcc atg cgc gct ttc ggc gcg aag gtt gag cgt gtg agc ccg gtc gcc      970
Ala Met Arg Ala Phe Gly Ala Lys Val Glu Arg Val Ser Pro Val Ala
210                 215                 220                 225 tgg cgc gtc gag ccc acc ggc tat cat gcg gcc gac ttc gtg atc gag     1018
Trp Arg Val Glu Pro Thr Gly Tyr His Ala Ala Asp Phe Val Ile Glu
                230                 235                 240 ccg gat gcc tct gct gcg acc tat ctc tgg gcc gcc gaa gtt ctg agc     1066
Pro Asp Ala Ser Ala Ala Thr Tyr Leu Trp Ala Ala Glu Val Leu Ser
            245                 250                 255 ggc ggc aag atc gat ctc ggc acg ccg gcg gaa cag ttc tcg caa ccg     1114
Gly Gly Lys Ile Asp Leu Gly Thr Pro Ala Glu Gln Phe Ser Gln Pro
        260                 265                 270 gat gcg aaa gcc tat gat ctg att tcg aaa ttc ccg cat ctg cct gct     1162
Asp Ala Lys Ala Tyr Asp Leu Ile Ser Lys Phe Pro His Leu Pro Ala
    275                 280                 285 gtc atc gac ggc tcg cag atg cag gac gcc atc ccg acg ctc gcc gtt     1210
Val Ile Asp Gly Ser Gln Met Gln Asp Ala Ile Pro Thr Leu Ala Val
290                 295                 300                 305 ctc gcc gct ttc aac gaa atg cct gtg cgc ttc gtc ggt atc gaa aac     1258
Leu Ala Ala Phe Asn Glu Met Pro Val Arg Phe Val Gly Ile Glu Asn
                310                 315                 320 ctg cgc gtc aag gaa tgc gat cgt atc cgc gcg ctc tcg agc ggc cta     1306
Leu Arg Val Lys Glu Cys Asp Arg Ile Arg Ala Leu Ser Ser Gly Leu
            325                 330                 335 tcc cgc atc gtt ccg aac ctc ggc acg gaa gag ggc gac gat ctc atc     1354
Ser Arg Ile Val Pro Asn Leu Gly Thr Glu Glu Gly Asp Asp Leu Ile
        340                 345                 350 atc gcc tcc gat ccg agc ctt gcc ggc aaa atc ctg acc gca gag atc     1402
Ile Ala Ser Asp Pro Ser Leu Ala Gly Lys Ile Leu Thr Ala Glu Ile
    355                 360                 365 gat agc ttt gcc gat cac cgc atc gcc atg agc ttt gcg ctg gcc ggc     1450
Asp Ser Phe Ala Asp His Arg Ile Ala Met Ser Phe Ala Leu Ala Gly
370                 375                 380                 385 ctg aag atc ggc ggc att acc att ctc gac ccc gac tgc gtc gcc aag     1498
Leu Lys Ile Gly Gly Ile Thr Ile Leu Asp Pro Asp Cys Val Ala Lys
                390                 395                 400 aca ttc ccg tcc tac tgg aat gtg ctg tct tcg ctg ggg gtc gcc tac     1546
Thr Phe Pro Ser Tyr Trp Asn Val Leu Ser Ser Leu Gly Val Ala Tyr
            405                 410                 415 gaa gac tga cgctctgctc ctatagaggc ctgagcgcgg atttattctt            1595
Glu Asp  * gacgcaaagc ggcgccggta acgggcgccgc aggcatcttt tggggaatg atgacacggc   1655 tctgcgggtt tttgctggcc ttgtgcctga tgctttgtgc aacggcggtg acggccgccg   1715
agctcatcag caattttgat caggcaattg cgttgcatcg tgatggctcc atgcgggtcg   1775
tcgaaacgat ttccgtcaat gccgaggggc gcgatatccg ccgcggcatc ttccgcgatt   1835
tcccgctgac cttcatcgat gcgaaaggcc gtgaaagcga ggttgatttt gcggtcgtct   1895
ccgtcgagcg cgacggcgag ccggaagaat ggcgtatcga acgcatcaaa ggcggtgagc   1955
gcatctatat cggcaatgcg caaacatttc tggatagcgg cctc                   2000
```

<210> SEQ ID NO 2
<211> LENGTH: 1257
<212> TYPE: DNA
<213> ORGANISM: Brevundomonas vesicularis
<220> FEATURE:
<221> NAME/KEY: CDS
<222> LOCATION: (1)...(1257)

<400> SEQUENCE: 2

```
atg atg atg ggt aga gcc aaa ctc acg att atc ccg ccg ggc aag cct      48
Met Met Met Gly Arg Ala Lys Leu Thr Ile Ile Pro Pro Gly Lys Pro
 1               5                  10                 15 ttg acc gga cgc gcc atg ccg ccg gga tcg aag tcg atc acc aac cgc      96
Leu Thr Gly Arg Ala Met Pro Pro Gly Ser Lys Ser Ile Thr Asn Arg
            20                  25                  30 gca ttg ctg ctc gcc ggc ctc gcc aag ggc acg agc cgg cta acc ggt     144
Ala Leu Leu Leu Ala Gly Leu Ala Lys Gly Thr Ser Arg Leu Thr Gly
        35                  40                  45 gcg ctg aag agc gac gat acc cgc tat atg gcc gaa gcg ctg cgt gcg     192
Ala Leu Lys Ser Asp Asp Thr Arg Tyr Met Ala Glu Ala Leu Arg Ala
 50                  55                  60 atg ggt gta acg atc gac gag ccc gac gac acc acg ttc atc gtc aaa     240
Met Gly Val Thr Ile Asp Glu Pro Asp Asp Thr Thr Phe Ile Val Lys
 65                  70                  75                  80 ggc agc ggc aag ctg cag ccg ccg gca gcc ccg ctt ttc ctc ggc aat     288
Gly Ser Gly Lys Leu Gln Pro Pro Ala Ala Pro Leu Phe Leu Gly Asn
                 85                  90                  95 gcc ggc acg gca acg cgc ttc ctg acg gcg gcc gcg gca ctg gtg gac     336
Ala Gly Thr Ala Thr Arg Phe Leu Thr Ala Ala Ala Ala Leu Val Asp
            100                 105                 110 ggc aag gtc atc gtc gac ggc gat gcc cat atg cgc aag cgg ccg atc     384
Gly Lys Val Ile Val Asp Gly Asp Ala His Met Arg Lys Arg Pro Ile
        115                 120                 125 gga ccg cta gtc gac gcg ttg cgc tcg ctc ggc atc gat gcc tcg gct     432
Gly Pro Leu Val Asp Ala Leu Arg Ser Leu Gly Ile Asp Ala Ser Ala
130                 135                 140 gaa acc ggc tgc ccg cca gtc acg atc aac ggc acc ggc cgc ttc gag     480
Glu Thr Gly Cys Pro Pro Val Thr Ile Asn Gly Thr Gly Arg Phe Glu
145                 150                 155                 160 gca agc cgc gtg cag atc gat ggc ggc ctg tcc agc cag tat gtc tcg     528
Ala Ser Arg Val Gln Ile Asp Gly Gly Leu Ser Ser Gln Tyr Val Ser
                165                 170                 175 gcg ctc ctg atg atg gcc gcc ggc ggc gat cgc gct gtc gat gtc gag     576
Ala Leu Leu Met Met Ala Ala Gly Gly Asp Arg Ala Val Asp Val Glu
            180                 185                 190 ctt ctc ggc gaa cat atc ggc gct ctc ggc tat atc gac ctg acc gtt     624
Leu Leu Gly Glu His Ile Gly Ala Leu Gly Tyr Ile Asp Leu Thr Val
        195                 200                 205 gcc gcc atg cgc gct ttc ggc gcg aag gtt gag cgt gtg agc ccg gtc     672
Ala Ala Met Arg Ala Phe Gly Ala Lys Val Glu Arg Val Ser Pro Val
210                 215                 220 gcc tgg cgc gtc gag ccc acc ggc tat cat gcg gcc gac ttc gtg atc     720
Ala Trp Arg Val Glu Pro Thr Gly Tyr His Ala Ala Asp Phe Val Ile
225                 230                 235                 240 gag ccg gat gcc tct gct gcg acc tat ctc tgg gcc gcc gaa gtt ctg     768
Glu Pro Asp Ala Ser Ala Ala Thr Tyr Leu Trp Ala Ala Glu Val Leu
                245                 250                 255 agc ggc ggc aag atc gat ctc ggc acg ccg gcg gaa cag ttc tcg caa     816
Ser Gly Gly Lys Ile Asp Leu Gly Thr Pro Ala Glu Gln Phe Ser Gln
            260                 265                 270 ccg gat gcg aaa gcc tat gat ctg att tcg aaa ttc ccg cat ctg cct     864
Pro Asp Ala Lys Ala Tyr Asp Leu Ile Ser Lys Phe Pro His Leu Pro
        275                 280                 285 gct gtc atc gac ggc tcg cag atg cag gac gcc atc ccg acg ctc gcc     912
Ala Val Ile Asp Gly Ser Gln Met Gln Asp Ala Ile Pro Thr Leu Ala
290                 295                 300 gtt ctc gcc gct ttc aac gaa atg cct gtg cgc ttc gtc ggt atc gaa     960
Val Leu Ala Ala Phe Asn Glu Met Pro Val Arg Phe Val Gly Ile Glu
```

```
                305                 310                 315                 320
aac ctg cgc gtc aag gaa tgc gat cgt atc cgc gcg ctc tcg agc ggc         1008
Asn Leu Arg Val Lys Glu Cys Asp Arg Ile Arg Ala Leu Ser Ser Gly
                325                 330                 335 cta tcc cgc atc gtt ccg aac ctc ggc acg gaa gag ggc gac gat ctc         1056
Leu Ser Arg Ile Val Pro Asn Leu Gly Thr Glu Glu Gly Asp Asp Leu
            340                 345                 350 atc atc gcc tcc gat ccg agc ctt gcc ggc aaa atc ctg acc gca gag         1104
Ile Ile Ala Ser Asp Pro Ser Leu Ala Gly Lys Ile Leu Thr Ala Glu
            355                 360                 365 atc gat agc ttt gcc gat cac cgc atc gcc atg agc ttt gcg ctg gcc         1152
Ile Asp Ser Phe Ala Asp His Arg Ile Ala Met Ser Phe Ala Leu Ala
        370                 375                 380 ggc ctg aag atc ggc ggc att acc att ctc gac ccc gac tgc gtc gcc         1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc         1248
Lys Thr Phe Pro Ser Tyr Trp Asn Val Leu Ser Ser Leu Gly Val Ala
            405                 410                 415 tac gaa gac                                                             1257
Tyr Glu Asp <210> SEQ ID NO 3
<211> LENGTH: 419
<212> TYPE: PRT
<213> ORGANISM: Brevundomonas vesicularis

<400> SEQUENCE: 3

Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Asp Thr Thr Phe Ile Val Lys
65                  70                  75                  80

Gly Ser Gly Lys Leu Gln Pro Pro Ala Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Asp Ala Leu Arg Ser Leu Gly Ile Asp Ala Ser Ala
    130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
            180                 185                 190

Leu Leu Gly Glu His Ile Gly Ala Leu Gly Tyr Ile Asp Leu Thr Val
        195                 200                 205

Ala Ala Met Arg Ala Phe Gly Ala Lys Val Glu Arg Val Ser Pro Val
    210                 215                 220
```

```
Ala Trp Arg Val Glu Pro Thr Gly Tyr His Ala Ala Asp Phe Val Ile
225                 230                 235                 240

Glu Pro Asp Ala Ser Ala Ala Thr Tyr Leu Trp Ala Ala Glu Val Leu
            245                 250                 255

Ser Gly Gly Lys Ile Asp Leu Gly Thr Pro Ala Glu Gln Phe Ser Gln
        260                 265                 270

Pro Asp Ala Lys Ala Tyr Asp Leu Ile Ser Lys Phe Pro His Leu Pro
    275                 280                 285

Ala Val Ile Asp Gly Ser Gln Met Gln Asp Ala Ile Pro Thr Leu Ala
290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Glu Gly Asp Asp Leu
            340                 345                 350

Ile Ile Ala Ser Asp Pro Ser Leu Ala Gly Lys Ile Leu Thr Ala Glu
        355                 360                 365

Ile Asp Ser Phe Ala Asp His Arg Ile Ala Met Ser Phe Ala Leu Ala
    370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
                405                 410                 415

Tyr Glu Asp

<210> SEQ ID NO 4
<211> LENGTH: 1260
<212> TYPE: DNA
<213> ORGANISM: Brevundomonas vesicularis
<220> FEATURE:
<221> NAME/KEY: CDS
<222> LOCATION: (1)...(1257)
<223> OTHER INFORMATION: grg8m1

<400> SEQUENCE: 4 atg atg atg ggt aga gcc aaa ctc acg att atc ccg ccg ggc aag cct      48
Met Met Met Gly Arg Ala Lys Leu Thr Ile Ile Pro Pro Gly Lys Pro
  1               5                  10                  15 ttg acc gga cgc gcc atg ccg ccg gga tcg aag tcg atc acc aac cgc      96
Leu Thr Gly Arg Ala Met Pro Pro Gly Ser Lys Ser Ile Thr Asn Arg
             20                  25                  30 gca ttg ctg ctc gcc ggc ctc gcc aag ggc acg agc cgg cta acc ggt     144
Ala Leu Leu Leu Ala Gly Leu Ala Lys Gly Thr Ser Arg Leu Thr Gly
         35                  40                  45 gcg ctg aag agc gac gat acc cgc tat atg gcc gaa gcg ctg cgt gcg     192
Ala Leu Lys Ser Asp Asp Thr Arg Tyr Met Ala Glu Ala Leu Arg Ala
     50                  55                  60 atg ggt gta acg atc gac gag ccc gac gac acc acg ttc atc gtc aaa     240
Met Gly Val Thr Ile Asp Glu Pro Asp Asp Thr Thr Phe Ile Val Lys
 65                  70                  75                  80 tgc agc ggc aag ctg cag ccg ccg gca gcc ccg ctt ttc ctc ggc aat     288
Cys Ser Gly Lys Leu Gln Pro Pro Ala Ala Pro Leu Phe Leu Gly Asn
                 85                  90                  95 gcc ggc acg gca acg cgc ttc ctg acg gcg gcc gcg ctg gtg gac         336
Ala Gly Thr Ala Thr Arg Phe Leu Thr Ala Ala Ala Leu Val Asp
            100                 105                 110 ggc aag gtc atc gtc gac ggc gat gcc cat atg cgc aag cgg ccg atc     384
Gly Lys Val Ile Val Asp Gly Asp Ala His Met Arg Lys Arg Pro Ile
```

-continued

```
        Gly Lys Val Ile Val Asp Gly Asp Ala His Met Arg Lys Arg Pro Ile
                115                 120                 125 gga ccg cta gtc gac gcg ttg cgc tcg ctc ggc atc gat gcc tcg gct         432
Gly Pro Leu Val Asp Ala Leu Arg Ser Leu Gly Ile Asp Ala Ser Ala
    130                 135                 140 gaa acc ggc tgc ccg cca gtc acg atc aac ggc acc ggc cgc ttc gag         480
Glu Thr Gly Cys Pro Pro Val Thr Ile Asn Gly Thr Gly Arg Phe Glu
145                 150                 155                 160 gca agc cgc gtg cag atc gat ggc ggc ctg tcc agc cag tat gtc tcg         528
Ala Ser Arg Val Gln Ile Asp Gly Gly Leu Ser Ser Gln Tyr Val Ser
                165                 170                 175 gcg ctc ctg atg atg gcc gcc ggc ggc gat cgc gct gtc gat gtc gag         576
Ala Leu Leu Met Met Ala Ala Gly Gly Asp Arg Ala Val Asp Val Glu
            180                 185                 190 ctt ctc ggc gaa cat atc ggc gct ctc ggc tat atc tac ctg acc gtt         624
Leu Leu Gly Glu His Ile Gly Ala Leu Gly Tyr Ile Tyr Leu Thr Val
        195                 200                 205 gcc gcc atg cgc gct ttc ggc gcg aag gtt gag cgt gtg agc ccg gtt         672
Ala Ala Met Arg Ala Phe Gly Ala Lys Val Glu Arg Val Ser Pro Val
    210                 215                 220 gcc tgg cgc ctc gag ccc acc ggc tat cat gcg gcc gac ttc gtg atc         720
Ala Trp Arg Leu Glu Pro Thr Gly Tyr His Ala Ala Asp Phe Val Ile
225                 230                 235                 240 gag ccg gat gcc tct gct gcg acc tat ctc tgg gcc gcc gaa gtt ctg         768
Glu Pro Asp Ala Ser Ala Ala Thr Tyr Leu Trp Ala Ala Glu Val Leu
                245                 250                 255 agc ggc ggc aag atc gat ctc ggc aca ccg gtg gaa cag ttc tcg caa         816
Ser Gly Gly Lys Ile Asp Leu Gly Thr Pro Val Glu Gln Phe Ser Gln
            260                 265                 270 ccg gat gcg aaa gcc tat gat ctg att tcg aaa ttc ccg cat ctg cct         864
Pro Asp Ala Lys Ala Tyr Asp Leu Ile Ser Lys Phe Pro His Leu Pro
        275                 280                 285 gct gtc atc tac ggc tcg cag atg cag gac gcc atc ccg acg ctc gcc         912
Ala Val Ile Tyr Gly Ser Gln Met Gln Asp Ala Ile Pro Thr Leu Ala
    290                 295                 300 gtt ctc gcc gct ttc aac gaa atg cct gtg cgc ttc gtc ggt atc gaa         960
Val Leu Ala Ala Phe Asn Glu Met Pro Val Arg Phe Val Gly Ile Glu
305                 310                 315                 320 aac ctg cgc gtc aag gaa tgc gat cgt atc cgc gcg ctc tcg agc ggc        1008
Asn Leu Arg Val Lys Glu Cys Asp Arg Ile Arg Ala Leu Ser Ser Gly
                325                 330                 335 cta tcc cgc atc gtt ccg aac ctc ggc acg gaa gag ggc gac gat ctc        1056
Leu Ser Arg Ile Val Pro Asn Leu Gly Thr Glu Glu Gly Asp Asp Leu
            340                 345                 350 atc atc gcc tcc gat ccg agc ctt gcc ggc aaa atc ctg acc gca gag        1104
Ile Ile Ala Ser Asp Pro Ser Leu Ala Gly Lys Ile Leu Thr Ala Glu
        355                 360                 365 atc gat agc ttt gcc gat cac cgc atc gcc atg agc ttt gcg ctg gcc        1152
Ile Asp Ser Phe Ala Asp His Arg Ile Ala Met Ser Phe Ala Leu Ala
    370                 375                 380 ggc ctg aag atc ggc ggc att acc att ctc gac ccc gac tgc gtc gcc        1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc        1248
Lys Thr Phe Pro Ser Tyr Trp Asn Val Leu Ser Ser Leu Gly Val Ala
                405                 410                 415 tac gaa gac tga                                                        1260
Tyr Glu Asp
```

<210> SEQ ID NO 5
<211> LENGTH: 419
<212> TYPE: PRT
<213> ORGANISM: Brevundomonas vesicularis
<220> FEATURE:
<221> NAME/KEY: VARIANT
<222> LOCATION: (0)...(0)
<223> OTHER INFORMATION: GR8m1

<400> SEQUENCE: 5

```
Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Asp Thr Thr Phe Ile Val Lys
65                  70                  75                  80

Cys Ser Gly Lys Leu Gln Pro Pro Ala Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Asp Ala Leu Arg Ser Leu Gly Ile Asp Ala Ser Ala
    130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
            180                 185                 190

Leu Leu Gly Glu His Ile Gly Ala Leu Gly Tyr Ile Tyr Leu Thr Val
        195                 200                 205

Ala Ala Met Arg Ala Phe Gly Ala Lys Val Glu Arg Val Ser Pro Val
    210                 215                 220

Ala Trp Arg Leu Glu Pro Thr Gly Tyr His Ala Ala Asp Phe Val Ile
225                 230                 235                 240

Glu Pro Asp Ala Ser Ala Ala Thr Tyr Leu Trp Ala Ala Glu Val Leu
                245                 250                 255

Ser Gly Gly Lys Ile Asp Leu Gly Thr Pro Val Glu Gln Phe Ser Gln
            260                 265                 270

Pro Asp Ala Lys Ala Tyr Asp Leu Ile Ser Lys Phe Pro His Leu Pro
        275                 280                 285

Ala Val Ile Tyr Gly Ser Gln Met Gln Asp Ala Ile Pro Thr Leu Ala
    290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Glu Gly Asp Asp Leu
            340                 345                 350

Ile Ile Ala Ser Asp Pro Ser Leu Ala Gly Lys Ile Leu Thr Ala Glu
        355                 360                 365
```

```
Ile Asp Ser Phe Ala Asp His Arg Ile Ala Met Ser Phe Ala Leu Ala
    370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
                405                 410                 415

Tyr Glu Asp

<210> SEQ ID NO 6
<211> LENGTH: 1260
<212> TYPE: DNA
<213> ORGANISM: Brevundomonas vesicularis
<220> FEATURE:
<221> NAME/KEY: CDS
<222> LOCATION: (1)...(1257)
<223> OTHER INFORMATION: grg8m2

<400> SEQUENCE: 6 atg atg atg ggt aga gcc aaa ctc acg att atc ccg ccg ggc aag cct     48
Met Met Met Gly Arg Ala Lys Leu Thr Ile Ile Pro Pro Gly Lys Pro
 1               5                  10                  15 ttg acc gga cgc gcc atg ccg ccg gga tcg aag tcg atc acc aac cgc     96
Leu Thr Gly Arg Ala Met Pro Pro Gly Ser Lys Ser Ile Thr Asn Arg
            20                  25                  30 gca ttg ctg ctc gcc ggc ctc gcc aag ggc acg agc cgg cta gcc ggt    144
Ala Leu Leu Leu Ala Gly Leu Ala Lys Gly Thr Ser Arg Leu Ala Gly
        35                  40                  45 gcg ctg aag agc gac gat acc cgc tat atg gcc gaa gcg ctg cgt gcg    192
Ala Leu Lys Ser Asp Asp Thr Arg Tyr Met Ala Glu Ala Leu Arg Ala
    50                  55                  60 atg ggt gta acg atc gac gag ccc gac gac acc atg ttc atc gtc aaa    240
Met Gly Val Thr Ile Asp Glu Pro Asp Asp Thr Met Phe Ile Val Lys
65                  70                  75                  80 ggc agc ggc aag ctg cag ccg ccg gca gcc ccg ctt ttc ctc ggc aat    288
Gly Ser Gly Lys Leu Gln Pro Pro Ala Ala Pro Leu Phe Leu Gly Asn
                85                  90                  95 gcc ggc acg gca acg cgc ttc ctg acg gcg gcc gcg gca ctg gtg gac    336
Ala Gly Thr Ala Thr Arg Phe Leu Thr Ala Ala Ala Ala Leu Val Asp
            100                 105                 110 ggc aag gtc atc gtc gac ggc gat gcc cat atg cgc aag cgg ccg atc    384
Gly Lys Val Ile Val Asp Gly Asp Ala His Met Arg Lys Arg Pro Ile
        115                 120                 125 gga ccg cta gtc gac gcg ttg cgc tcg ctc ggc atc gat gcc tcg gct    432
Gly Pro Leu Val Asp Ala Leu Arg Ser Leu Gly Ile Asp Ala Ser Ala
    130                 135                 140 gaa acc ggc tgc ccg cca gtc acg atc aac ggc acc ggc cgc ttc gag    480
Glu Thr Gly Cys Pro Pro Val Thr Ile Asn Gly Thr Gly Arg Phe Glu
145                 150                 155                 160 gca agc cgc gtg cag atc gat ggc ggc ctg tcc agc cag tat gtc tcg    528
Ala Ser Arg Val Gln Ile Asp Gly Gly Leu Ser Ser Gln Tyr Val Ser
                165                 170                 175 gcg ctc ctg atg atg gcc gcc ggc ggc gat cgc gct gtc gat gtc gag    576
Ala Leu Leu Met Met Ala Ala Gly Gly Asp Arg Ala Val Asp Val Glu
            180                 185                 190 ctt ctc agc gaa cat atc ggc gct ctc ggc tat atc gac ctg acc gtt    624
Leu Leu Ser Glu His Ile Gly Ala Leu Gly Tyr Ile Asp Leu Thr Val
        195                 200                 205 gcc gcc atg cgc gct ttc ggc gcg aag gtt gag cgt gtg agc ccg gtc    672
Ala Ala Met Arg Ala Phe Gly Ala Lys Val Glu Arg Val Ser Pro Val
    210                 215                 220
```

```
gcc tgg cgc gtc gag ccc acc ggc tat cat gcg gcc gac ttc gtg atc      720
Ala Trp Arg Val Glu Pro Thr Gly Tyr His Ala Ala Asp Phe Val Ile
225                 230                 235                 240 gag ccg gat gcc tct gct gcg acc tat ctc tgg gcc gcc gaa gtt ctg      768
Glu Pro Asp Ala Ser Ala Ala Thr Tyr Leu Trp Ala Ala Glu Val Leu
                245                 250                 255 agc ggc ggc aag atc gat ctc ggc acg ccg gcg gaa cag ttc tcg caa      816
Ser Gly Gly Lys Ile Asp Leu Gly Thr Pro Ala Glu Gln Phe Ser Gln
            260                 265                 270 ccg gat gcg aaa gcc tat gat ctg att tcg aaa ttc ccg cat ctg cct      864
Pro Asp Ala Lys Ala Tyr Asp Leu Ile Ser Lys Phe Pro His Leu Pro
        275                 280                 285 gct gtc atc gac agc tcg cag atg cag gac gcc atc ccg acg ctc gcc      912
Ala Val Ile Asp Ser Ser Gln Met Gln Asp Ala Ile Pro Thr Leu Ala
    290                 295                 300 gtt ctc gcc gct ttc aac gaa atg cct gtg cgc ttc gtc ggt atc gaa      960
Val Leu Ala Ala Phe Asn Glu Met Pro Val Arg Phe Val Gly Ile Glu
305                 310                 315                 320 aac ctg cgc gtc aag gaa tgc gat cgt atc cgc gcg ctc tcg agc ggc     1008
Asn Leu Arg Val Lys Glu Cys Asp Arg Ile Arg Ala Leu Ser Ser Gly
                325                 330                 335 cta tcc cgc atc gtt ccg aac ctc ggc acg gaa gag ggc gac gat ctc     1056
Leu Ser Arg Ile Val Pro Asn Leu Gly Thr Glu Glu Gly Asp Asp Leu
            340                 345                 350 atc atc gcc tcc gat ccg agc ctt gcc ggc aaa atc ctg acc gca gag     1104
Ile Ile Ala Ser Asp Pro Ser Leu Ala Gly Lys Ile Leu Thr Ala Glu
        355                 360                 365 atc gat agc ttt gcc gat cac cgc atc gcc atg agc ttt gcg ctg gcc     1152
Ile Asp Ser Phe Ala Asp His Arg Ile Ala Met Ser Phe Ala Leu Ala
    370                 375                 380 ggc ctg aag atc ggc ggc att acc att ctc gac ccc gac tgc gtc gcc     1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc     1248
Lys Thr Phe Pro Ser Tyr Trp Asn Val Leu Ser Ser Leu Gly Val Ala
                405                 410                 415 tac gaa gac tga                                                     1260
Tyr Glu Asp <210> SEQ ID NO 7
<211> LENGTH: 419
<212> TYPE: PRT
<213> ORGANISM: Brevundomonas vesicularis
<220> FEATURE:
<221> NAME/KEY: VARIANT
<222> LOCATION: (0)...(0)
<223> OTHER INFORMATION: GRG8m2

<400> SEQUENCE: 7

Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Ala Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Asp Thr Met Phe Ile Val Lys
65                  70                  75                  80
```

```
Gly Ser Gly Lys Leu Gln Pro Pro Ala Ala Pro Leu Phe Leu Gly Asn
            85                  90                  95

Ala Gly Thr Ala Thr Arg Phe Leu Thr Ala Ala Ala Ala Leu Val Asp
            100                 105                 110

Gly Lys Val Ile Val Asp Gly Asp Ala His Met Arg Lys Arg Pro Ile
            115                 120                 125

Gly Pro Leu Val Asp Ala Leu Arg Ser Leu Gly Ile Asp Ala Ser Ala
            130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
            165                 170                 175

Ala Leu Leu Met Met Ala Ala Gly Gly Asp Arg Ala Val Asp Val Glu
            180                 185                 190

Leu Leu Ser Glu His Ile Gly Ala Leu Gly Tyr Ile Asp Leu Thr Val
            195                 200                 205

Ala Ala Met Arg Ala Phe Gly Ala Lys Val Glu Arg Val Ser Pro Val
            210                 215                 220

Ala Trp Arg Val Glu Pro Thr Gly Tyr His Ala Ala Asp Phe Val Ile
225                 230                 235                 240

Glu Pro Asp Ala Ser Ala Ala Thr Tyr Leu Trp Ala Ala Glu Val Leu
            245                 250                 255

Ser Gly Gly Lys Ile Asp Leu Gly Thr Pro Ala Glu Gln Phe Ser Gln
            260                 265                 270

Pro Asp Ala Lys Ala Tyr Asp Leu Ile Ser Lys Phe Pro His Leu Pro
            275                 280                 285

Ala Val Ile Asp Ser Ser Gln Met Gln Asp Ala Ile Pro Thr Leu Ala
            290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
            325                 330                 335

Leu Ser Arg Ile Val Pro Asn Leu Gly Thr Glu Glu Gly Asp Asp Leu
            340                 345                 350

Ile Ile Ala Ser Asp Pro Ser Leu Ala Gly Lys Ile Leu Thr Ala Glu
            355                 360                 365

Ile Asp Ser Phe Ala Asp His Arg Ile Ala Met Ser Phe Ala Leu Ala
            370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
            405                 410                 415

Tyr Glu Asp

<210> SEQ ID NO 8
<211> LENGTH: 1260
<212> TYPE: DNA
<213> ORGANISM: Brevundomonas vesicularis
<220> FEATURE:
<221> NAME/KEY: CDS
<222> LOCATION: (1)...(1257)
<223> OTHER INFORMATION: grg8m3

<400> SEQUENCE: 8 atg atg atg ggt aga gcc aaa ctc acg att atc ccg ccg ggc aag cct      48
Met Met Met Gly Arg Ala Lys Leu Thr Ile Ile Pro Pro Gly Lys Pro
```

```
                                        -continued
  1            5              10             15
ttg acc gga cgc gcc atg tcg ccg gga tcg aag tcg atc acc aac cgc      96
Leu Thr Gly Arg Ala Met Ser Pro Gly Ser Lys Ser Ile Thr Asn Arg
            20             25             30 gca ttg ctg ctc gcc ggc ctc gcc aag ggc acg agc cgg cta acc ggt     144
Ala Leu Leu Leu Ala Gly Leu Ala Lys Gly Thr Ser Arg Leu Thr Gly
            35             40             45 gcg ctg aag agc gac gat acc cgc tat atg gcc gaa gcg ctg cgt gcg    192
Ala Leu Lys Ser Asp Asp Thr Arg Tyr Met Ala Glu Ala Leu Arg Ala
        50             55             60 atg ggt gta acg atc gac gag ccc gac gac acc acg ttc atc gtc aaa    240
Met Gly Val Thr Ile Asp Glu Pro Asp Asp Thr Thr Phe Ile Val Lys
65             70             75             80 ggc agc ggc aag ctg cag ccg ccg gca gcc ccg ctt ttc ctc ggc aat    288
Gly Ser Gly Lys Leu Gln Pro Pro Ala Ala Pro Leu Phe Leu Gly Asn
            85             90             95 gcc ggc acg gca acg cgc ttc ctg acg gcg gcc gcg gca ctg gtg gac    336
Ala Gly Thr Ala Thr Arg Phe Leu Thr Ala Ala Ala Leu Val Asp
            100            105            110 ggc aag gtc atc gtc gac ggc gat gcc cat atg cgc aag cgg ccg atc    384
Gly Lys Val Ile Val Asp Gly Asp Ala His Met Arg Lys Arg Pro Ile
            115            120            125 gga ccg cta gtc gac gcg ttg cgc tcg ctc ggc atc gat gcc tcg gct    432
Gly Pro Leu Val Asp Ala Leu Arg Ser Leu Gly Ile Asp Ala Ser Ala
        130            135            140 gaa acc ggc tgc ccg cca gtc acg atc aac ggc acc ggc cgc ttc gag    480
Glu Thr Gly Cys Pro Pro Val Thr Ile Asn Gly Thr Gly Arg Phe Glu
145            150            155            160 gca agc cgc gtg cag atc gat ggc ggc ctg tcc agc cag tat gtc tcg    528
Ala Ser Arg Val Gln Ile Asp Gly Gly Leu Ser Ser Gln Tyr Val Ser
            165            170            175 gcg ctc ctg atg atg gcc gcc ggc ggt gat cgc gct gtc gat gtc gag    576
Ala Leu Leu Met Met Ala Ala Gly Gly Asp Arg Ala Val Asp Val Glu
            180            185            190 ctt ctc ggc gaa cat atc ggc gct ctc ggc tat atc gac ctg acc gtt    624
Leu Leu Gly Glu His Ile Gly Ala Leu Gly Tyr Ile Asp Leu Thr Val
            195            200            205 gcc gcc atg cgc gct ttc ggc gcg aag gtt gag cgt gtg agc ccg gtc    672
Ala Ala Met Arg Ala Phe Gly Ala Lys Val Glu Arg Val Ser Pro Val
        210            215            220 gcc tgg cgc gtc gag ccc acc ggc tat cat gcg gcc gac ttc gtg atc    720
Ala Trp Arg Val Glu Pro Thr Gly Tyr His Ala Ala Asp Phe Val Ile
225            230            235            240 gag ccg gat gcc tct gct gcg acc ttt ctc tgg gcc gcc gaa gtt ctg    768
Glu Pro Asp Ala Ser Ala Ala Thr Phe Leu Trp Ala Ala Glu Val Leu
            245            250            255 agc ggc ggc aag atc gat ctc ggc atg ccg gcg gaa cag ttc tcg caa    816
Ser Gly Gly Lys Ile Asp Leu Gly Met Pro Ala Glu Gln Phe Ser Gln
            260            265            270 ccg gat gcg aaa gcc tat gat ctg att tcg aaa ttc ccg cat ctg cct    864
Pro Asp Ala Lys Ala Tyr Asp Leu Ile Ser Lys Phe Pro His Leu Pro
        275            280            285 gct gtc atc gac ggc tcg cag atg cag gac gcc atc ccg acg ctc gcc    912
Ala Val Ile Asp Gly Ser Gln Met Gln Asp Ala Ile Pro Thr Leu Ala
            290            295            300 gtt ctc gcc gct ttc aac gaa atg cct gtg cgc ttc gtc ggt atc gaa    960
Val Leu Ala Ala Phe Asn Glu Met Pro Val Arg Phe Val Gly Ile Glu
305            310            315            320 aac ctg cgc gtc aag gaa tgc gat cgt atc cgc gcg ctc tcg agc ggc   1008
```

```
                                                      -continued

Asn Leu Arg Val Lys Glu Cys Asp Arg Ile Arg Ala Leu Ser Ser Gly
                325                 330                 335 cta tcc cgc atc gtt ccg aac ctc ggc acg gaa gag ggc gac gat ctc      1056
Leu Ser Arg Ile Val Pro Asn Leu Gly Thr Glu Glu Gly Asp Asp Leu
            340                 345                 350 atc atc gcc tct gat ccg agc ctt gcc ggc aaa atc ctg acc gca gag      1104
Ile Ile Ala Ser Asp Pro Ser Leu Ala Gly Lys Ile Leu Thr Ala Glu
            355                 360                 365 atc gat agc ttt gcc gat cac cgt atc gcc atg agc ttt gcg ctg gcc      1152
Ile Asp Ser Phe Ala Asp His Arg Ile Ala Met Ser Phe Ala Leu Ala
370                 375                 380 ggc ctg aag atc ggc ggc att acc att ctc gac ccc gac tgc gtc gcc      1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc      1248
Lys Thr Phe Pro Ser Tyr Trp Asn Val Leu Ser Ser Leu Gly Val Ala
                405                 410                 415 tac gaa gac tga                                                      1260
Tyr Glu Asp <210> SEQ ID NO 9
<211> LENGTH: 419
<212> TYPE: PRT
<213> ORGANISM: Brevundomonas vesicularis
<220> FEATURE:
<221> NAME/KEY: VARIANT
<222> LOCATION: (0)...(0)
<223> OTHER INFORMATION: GRG8m3

<400> SEQUENCE: 9

Met Met Met Gly Arg Ala Lys Leu Thr Ile Ile Pro Pro Gly Lys Pro
1               5                   10                  15

Leu Thr Gly Arg Ala Met Ser Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Asp Thr Thr Phe Ile Val Lys
65                  70                  75                  80

Gly Ser Gly Lys Leu Gln Pro Pro Ala Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Asp Ala Leu Arg Ser Leu Gly Ile Asp Ala Ser Ala
    130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
            180                 185                 190

Leu Leu Gly Glu His Ile Gly Ala Leu Gly Tyr Ile Asp Leu Thr Val
        195                 200                 205

Ala Ala Met Arg Ala Phe Gly Ala Lys Val Glu Arg Val Ser Pro Val
    210                 215                 220
```

```
Ala Trp Arg Val Glu Pro Thr Gly Tyr His Ala Asp Phe Val Ile
225                 230                 235                 240

Glu Pro Asp Ala Ser Ala Ala Thr Phe Leu Trp Ala Ala Glu Val Leu
            245                 250                 255

Ser Gly Gly Lys Ile Asp Leu Gly Met Pro Ala Glu Gln Phe Ser Gln
                260                 265                 270

Pro Asp Ala Lys Ala Tyr Asp Leu Ile Ser Lys Phe Pro His Leu Pro
            275                 280                 285

Ala Val Ile Asp Gly Ser Gln Met Gln Asp Ala Ile Pro Thr Leu Ala
        290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Glu Gly Asp Asp Leu
                340                 345                 350

Ile Ile Ala Ser Asp Pro Ser Leu Ala Gly Lys Ile Leu Thr Ala Glu
        355                 360                 365

Ile Asp Ser Phe Ala Asp His Arg Ile Ala Met Ser Phe Ala Leu Ala
        370                 375                 380

Gly Leu Lys Ile Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
                405                 410                 415

Tyr Glu Asp

<210> SEQ ID NO 10
<211> LENGTH: 1260
<212> TYPE: DNA
<213> ORGANISM: Brevundomonas vesicularis
<220> FEATURE:
<221> NAME/KEY: CDS
<222> LOCATION: (1)...(1257)
<223> OTHER INFORMATION: grg8m4

<400> SEQUENCE: 10 atg atg atg ggt aga gcc aaa ctc acg att atc ccg ccg ggc aag cct      48
Met Met Met Gly Arg Ala Lys Leu Thr Ile Ile Pro Pro Gly Lys Pro
1               5                   10                  15 ttg acc gga cgc gcc atg ccg ccg gga tcg aag tcg atc acc aac cgc      96
Leu Thr Gly Arg Ala Met Pro Pro Gly Ser Lys Ser Ile Thr Asn Arg
            20                  25                  30 gca ttg ctg ctc gcc ggc ctc gcc aag ggc acg agc cgg cta acc ggt     144
Ala Leu Leu Leu Ala Gly Leu Ala Lys Gly Thr Ser Arg Leu Thr Gly
        35                  40                  45 gcg ctg aag agc gac gat acc cgc tat atg gcc gaa gcg ctg cgt gcg     192
Ala Leu Lys Ser Asp Asp Thr Arg Tyr Met Ala Glu Ala Leu Arg Ala
    50                  55                  60 atg ggt gta acg atc gac gag ccc gac tac acc acg ttc atc gtc aaa     240
Met Gly Val Thr Ile Asp Glu Pro Asp Tyr Thr Thr Phe Ile Val Lys
65                  70                  75                  80 ggc agc ggc aag ctg cag ccg ccg gca gcc ccg ctt ttc ctc ggc aat     288
Gly Ser Gly Lys Leu Gln Pro Pro Ala Ala Pro Leu Phe Leu Gly Asn
                85                  90                  95 gcc ggc acg gca acg cgc ttc ctg acg gcg gcc gcg gca ctg gtg gac     336
Ala Gly Thr Ala Thr Arg Phe Leu Thr Ala Ala Ala Leu Val Asp
            100                 105                 110
```

```
ggc aag gtc atc gtc gac ggc gat gcc cat atg cgc aag cgg ccg atc         384
Gly Lys Val Ile Val Asp Gly Asp Ala His Met Arg Lys Arg Pro Ile
        115                 120                 125 gga ccg cta gtc gac gcg ttg cgc tcg ctc ggc atc gat gcc tcg gct         432
Gly Pro Leu Val Asp Ala Leu Arg Ser Leu Gly Ile Asp Ala Ser Ala
130                 135                 140 gaa acc ggc tgc ccg cca gtc acg atc aac ggc acc ggc cgc ttc gag         480
Glu Thr Gly Cys Pro Pro Val Thr Ile Asn Gly Thr Gly Arg Phe Glu
145                 150                 155                 160 gca agc cgc gtg cag atc gat ggc ggc ctg tcc agc cag tat gtc tcg         528
Ala Ser Arg Val Gln Ile Asp Gly Gly Leu Ser Ser Gln Tyr Val Ser
                165                 170                 175 gcg ctc ctg atg atg gcc gcc ggc ggc gat cgc gct gtc gat gtc gag         576
Ala Leu Leu Met Met Ala Ala Gly Gly Asp Arg Ala Val Asp Val Glu
            180                 185                 190 ctt ctc ggc gaa cat atc ggc gct ctc ggc tat atc gac ctg acc gtt         624
Leu Leu Gly Glu His Ile Gly Ala Leu Gly Tyr Ile Asp Leu Thr Val
        195                 200                 205 gcc gtc atg cgc gct ttc ggc gcg aag gtt gag cgt gtg agc ccg gtc         672
Ala Val Met Arg Ala Phe Gly Ala Lys Val Glu Arg Val Ser Pro Val
210                 215                 220 gcc tgg cgc gtc gag ccc acc ggc tat cat gcg gtc gac ttc gtg atc         720
Ala Trp Arg Val Glu Pro Thr Gly Tyr His Ala Val Asp Phe Val Ile
225                 230                 235                 240 gag ccg gat gcc tct gct gcg acc tat ctc tgg gcc gcc gaa gtt ctg         768
Glu Pro Asp Ala Ser Ala Ala Thr Tyr Leu Trp Ala Ala Glu Val Leu
                245                 250                 255 agc ggc ggc aag atc gat ctc ggc acg ccg gcg gaa cag ttc tcg caa         816
Ser Gly Gly Lys Ile Asp Leu Gly Thr Pro Ala Glu Gln Phe Ser Gln
            260                 265                 270 ccg gat gcg aaa gcc tat gat ctg att tcg aaa ttc ccg cat ctg cct         864
Pro Asp Ala Lys Ala Tyr Asp Leu Ile Ser Lys Phe Pro His Leu Pro
        275                 280                 285 gct gtc atc gac ggc tcg cag atg cag gac gcc atc ccg acg ctc gcc         912
Ala Val Ile Asp Gly Ser Gln Met Gln Asp Ala Ile Pro Thr Leu Ala
290                 295                 300 gtt ctc gcc gct ttc aac gaa atg cct gtg cgc ttc gtc ggt atc gaa         960
Val Leu Ala Ala Phe Asn Glu Met Pro Val Arg Phe Val Gly Ile Glu
305                 310                 315                 320 aac ctg cgc gtc aag gaa tgc gat cgt atc cgc gcg ctc tcg agc ggc        1008
Asn Leu Arg Val Lys Glu Cys Asp Arg Ile Arg Ala Leu Ser Ser Gly
                325                 330                 335 cta tcc cgc atc gtt ccg aac ctc ggc acg gaa gag ggc gac gat ctc        1056
Leu Ser Arg Ile Val Pro Asn Leu Gly Thr Glu Glu Gly Asp Asp Leu
            340                 345                 350 atc atc gcc tcc gat ccg agc ctt gcc ggc aaa atc ctg acc gca gag        1104
Ile Ile Ala Ser Asp Pro Ser Leu Ala Gly Lys Ile Leu Thr Ala Glu
        355                 360                 365 atc gat agc ttt gcc gat cac cgc atc gcc atg agc ttt gcg ctg gcc        1152
Ile Asp Ser Phe Ala Asp His Arg Ile Ala Met Ser Phe Ala Leu Ala
370                 375                 380 ggc ctg aag atc ggc ggc att acc att ctc gac ccc gac tgc gtc gcc        1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc        1248
Lys Thr Phe Pro Ser Tyr Trp Asn Val Leu Ser Ser Leu Gly Val Ala
                405                 410                 415 tac gaa gac tga                                                        1260
Tyr Glu Asp
```

<210> SEQ ID NO 11
<211> LENGTH: 419
<212> TYPE: PRT
<213> ORGANISM: Brevundomonas vesicularis
<220> FEATURE:
<221> NAME/KEY: VARIANT
<222> LOCATION: (0)...(0)
<223> OTHER INFORMATION: GRG8m4

<400> SEQUENCE: 11

```
Met Met Met Gly Arg Ala Lys Leu Thr Ile Ile Pro Pro Gly Lys Pro
 1               5                  10                  15

Leu Thr Gly Arg Ala Met Pro Pro Gly Ser Lys Ser Ile Thr Asn Arg
                20                  25                  30

Ala Leu Leu Leu Ala Gly Leu Ala Lys Gly Thr Ser Arg Leu Thr Gly
            35                  40                  45

Ala Leu Lys Ser Asp Asp Thr Arg Tyr Met Ala Glu Ala Leu Arg Ala
        50                  55                  60

Met Gly Val Thr Ile Asp Glu Pro Tyr Asp Thr Thr Phe Ile Val Lys
65                  70                  75                  80

Gly Ser Gly Lys Leu Gln Pro Pro Ala Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Asp Ala Leu Arg Ser Leu Gly Ile Asp Ala Ser Ala
130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
            180                 185                 190

Leu Leu Gly Glu His Ile Gly Ala Leu Gly Tyr Ile Asp Leu Thr Val
        195                 200                 205

Val Ala Met Arg Ala Phe Gly Ala Lys Val Glu Arg Val Ser Pro Val
210                 215                 220

Ala Trp Arg Val Glu Pro Thr Gly Tyr His Val Ala Asp Phe Val Ile
225                 230                 235                 240

Glu Pro Asp Ala Ser Ala Ala Thr Tyr Leu Trp Ala Ala Glu Val Leu
                245                 250                 255

Ser Gly Gly Lys Ile Asp Leu Gly Thr Pro Ala Glu Gln Phe Ser Gln
            260                 265                 270

Pro Asp Ala Lys Ala Tyr Asp Leu Ile Ser Lys Phe Pro His Leu Pro
        275                 280                 285

Ala Val Ile Asp Gly Ser Gln Met Gln Asp Ala Ile Pro Thr Leu Ala
290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Glu Gly Asp Asp Leu
            340                 345                 350

Ile Ile Ala Ser Asp Pro Ser Leu Ala Gly Lys Ile Leu Thr Ala Glu
```

-continued

```
            355                 360                 365
Ile Asp Ser Phe Ala Asp His Arg Ile Ala Met Ser Phe Ala Leu Ala
        370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
                405                 410                 415

Tyr Glu Asp

<210> SEQ ID NO 12
<211> LENGTH: 1260
<212> TYPE: DNA
<213> ORGANISM: Brevundomonas vesicularis
<220> FEATURE:
<221> NAME/KEY: CDS
<222> LOCATION: (1)...(1257)
<223> OTHER INFORMATION: grg8m5

<400> SEQUENCE: 12 atg atg atg ggt aga gcc aaa ctc acg att atc ccg ccg ggc aag cct     48
Met Met Met Gly Arg Ala Lys Leu Thr Ile Ile Pro Pro Gly Lys Pro
 1               5                  10                  15 ttg acc gga cgc gcc atg ccg ccg gga tcg aag tcg atc acc aac cgc     96
Leu Thr Gly Arg Ala Met Pro Pro Gly Ser Lys Ser Ile Thr Asn Arg
                20                  25                  30 gca ttg ctg ctc gcc ggc ctc gcc aag ggc acg agc cgg cta acc ggt    144
Ala Leu Leu Leu Ala Gly Leu Ala Lys Gly Thr Ser Arg Leu Thr Gly
            35                  40                  45 gcg ctg aag agc gac gat acc cgc tat atg gcc gaa gcg ctg cgt gcg    192
Ala Leu Lys Ser Asp Asp Thr Arg Tyr Met Ala Glu Ala Leu Arg Ala
        50                  55                  60 atg ggt gta acg atc gac gag ccc gac gac acc acg ttc atc gtc aaa    240
Met Gly Val Thr Ile Asp Glu Pro Asp Asp Thr Thr Phe Ile Val Lys
65                  70                  75                  80 ggc agc ggc aag ctg cag ccg ccg gca gcc ccg ctt ttc ctc ggc aat    288
Gly Ser Gly Lys Leu Gln Pro Pro Ala Ala Pro Leu Phe Leu Gly Asn
                85                  90                  95 gcc ggc acg gca acg cgc ttc ctg acg gcg gcc gcg gca ctg gtg gac    336
Ala Gly Thr Ala Thr Arg Phe Leu Thr Ala Ala Ala Leu Val Asp
                100                 105                 110 ggc aag gtc atc gtc gac ggc gat gcc cat atg cgc aag cgg ccg atc    384
Gly Lys Val Ile Val Asp Gly Asp Ala His Met Arg Lys Arg Pro Ile
            115                 120                 125 gga ccg cta gtc gag gcg ttg cgc tcg ctc gac atc gat gcc tcg gct    432
Gly Pro Leu Val Glu Ala Leu Arg Ser Leu Asp Ile Asp Ala Ser Ala
        130                 135                 140 gaa acc ggc tgc ccg cca gtc acg atc aac ggc acc ggc cgc ttc gag    480
Glu Thr Gly Cys Pro Pro Val Thr Ile Asn Gly Thr Gly Arg Phe Glu
145                 150                 155                 160 gca agc cgc gtg cag atc gat ggc ggc ctg tcc agc cag tat gtc tcg    528
Ala Ser Arg Val Gln Ile Asp Gly Gly Leu Ser Ser Gln Tyr Val Ser
                165                 170                 175 gcg ctc ctg atg atg gcc gcc ggc ggc gat cgc gct gtc gat gtc gag    576
Ala Leu Leu Met Met Ala Ala Gly Gly Asp Arg Ala Val Asp Val Glu
                180                 185                 190 ctt ctc ggc gaa cat atc ggc gct ctt ggc tat atc gac ctg acc gtt    624
Leu Leu Gly Glu His Ile Gly Ala Leu Gly Tyr Ile Asp Leu Thr Val
            195                 200                 205 gcc gcc atg cgc gct ttc ggc gcg aag gtt gag cgt gtg agc ccg gtc    672
Ala Ala Met Arg Ala Phe Gly Ala Lys Val Glu Arg Val Ser Pro Val
```

```
       210                 215                 220
acc tgg cgc gtc gag ccc acc ggc tat cat gcg gcc gac ttc gtg atc          720
Thr Trp Arg Val Glu Pro Thr Gly Tyr His Ala Ala Asp Phe Val Ile
225                 230                 235                 240 gag ccg gat gcc tct gct gcg acc tat ctc tgg gcc gcc gaa gtt ctg          768
Glu Pro Asp Ala Ser Ala Ala Thr Tyr Leu Trp Ala Ala Glu Val Leu
                245                 250                 255 agc ggc ggc aag atc gat ctc ggc acg ccg gcg gaa cag ttc tcg caa          816
Ser Gly Gly Lys Ile Asp Leu Gly Thr Pro Ala Glu Gln Phe Ser Gln
            260                 265                 270 ccg gat gcg aaa gcc tat gat ctg att tcg aaa ttc ccg cat ctg cct          864
Pro Asp Ala Lys Ala Tyr Asp Leu Ile Ser Lys Phe Pro His Leu Pro
        275                 280                 285 gct gtc atc gac ggc tcg cag atg cag gac gcc atc ccg acg ctc gcc          912
Ala Val Ile Asp Gly Ser Gln Met Gln Asp Ala Ile Pro Thr Leu Ala
    290                 295                 300 gtt ctc gct gct ttc aac gaa atg cct gtg cgc ttc gtc ggt atc gaa          960
Val Leu Ala Ala Phe Asn Glu Met Pro Val Arg Phe Val Gly Ile Glu
305                 310                 315                 320 aac ctg cgc gtc aag gaa tgc gat cgt atc cgc gcg ctc tcg agc ggc         1008
Asn Leu Arg Val Lys Glu Cys Asp Arg Ile Arg Ala Leu Ser Ser Gly
                325                 330                 335 cta tcc cgc atc gtt ccg aac ctc ggc acg gaa gag ggc gac gat ctc         1056
Leu Ser Arg Ile Val Pro Asn Leu Gly Thr Glu Glu Gly Asp Asp Leu
            340                 345                 350 atc atc tcc tcc gat ccg agc ctt gcc ggc aaa aac ctg acc gca gag         1104
Ile Ile Ser Ser Asp Pro Ser Leu Ala Gly Lys Asn Leu Thr Ala Glu
        355                 360                 365 atc gat agc ttt gcc gat cac cgc atc gcc atg agc ttt gcg ctg gcc         1152
Ile Asp Ser Phe Ala Asp His Arg Ile Ala Met Ser Phe Ala Leu Ala
    370                 375                 380 ggc ctg aag atc ggc ggc att acc att ctc gac cct gac tgc gtc gcc         1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc         1248
Lys Thr Phe Pro Ser Tyr Trp Asn Val Leu Ser Ser Leu Gly Val Ala
                405                 410                 415 tac gaa gac tga                                                         1260
Tyr Glu Asp <210> SEQ ID NO 13
<211> LENGTH: 419
<212> TYPE: PRT
<213> ORGANISM: Brevundomonas vesicularis
<220> FEATURE:
<221> NAME/KEY: VARIANT
<222> LOCATION: (0)...(0)
<223> OTHER INFORMATION: GRG8m5

<400> SEQUENCE: 13

Met Met Met Gly Arg Ala Lys Leu Thr Ile Pro Pro Gly Lys Pro
1               5                   10                  15

Leu Thr Gly Arg Ala Met Pro Pro Gly Ser Lys Ser Ile Thr Asn Arg
                20                  25                  30

Ala Leu Leu Leu Ala Gly Leu Ala Lys Gly Thr Ser Arg Leu Thr Gly
            35                  40                  45

Ala Leu Lys Ser Asp Asp Thr Arg Tyr Met Ala Glu Ala Leu Arg Ala
        50                  55                  60

Met Gly Val Thr Ile Asp Glu Pro Asp Thr Thr Phe Ile Val Lys
65                  70                  75                  80
```

```
Gly Ser Gly Lys Leu Gln Pro Ala Ala Pro Leu Phe Leu Gly Asn
                 85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Glu Ala Leu Arg Ser Leu Asp Ile Asp Ala Ser Ala
    130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
            180                 185                 190

Leu Leu Gly Glu His Ile Gly Ala Leu Gly Tyr Ile Asp Leu Thr Val
        195                 200                 205

Ala Ala Met Arg Ala Phe Gly Ala Lys Val Glu Arg Val Ser Pro Val
    210                 215                 220

Thr Trp Arg Val Glu Pro Thr Gly Tyr His Ala Ala Asp Phe Val Ile
225                 230                 235                 240

Glu Pro Asp Ala Ser Ala Ala Thr Tyr Leu Trp Ala Ala Glu Val Leu
                245                 250                 255

Ser Gly Gly Lys Ile Asp Leu Gly Thr Pro Ala Glu Gln Phe Ser Gln
            260                 265                 270

Pro Asp Ala Lys Ala Tyr Asp Leu Ile Ser Lys Phe Pro His Leu Pro
        275                 280                 285

Ala Val Ile Asp Gly Ser Gln Met Gln Asp Ala Ile Pro Thr Leu Ala
    290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Gly Asp Asp Leu
            340                 345                 350

Ile Ile Ser Ser Asp Pro Ser Leu Ala Gly Lys Asn Leu Thr Ala Glu
        355                 360                 365

Ile Asp Ser Phe Ala Asp His Arg Ile Ala Met Ser Phe Ala Leu Ala
    370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
                405                 410                 415

Tyr Glu Asp

<210> SEQ ID NO 14
<211> LENGTH: 1260
<212> TYPE: DNA
<213> ORGANISM: Brevundomonas vesicularis
<220> FEATURE:
<221> NAME/KEY: CDS
<222> LOCATION: (1)...(1257)
<223> OTHER INFORMATION: grg8m6

<400> SEQUENCE: 14 atg atg atg gat aga gcc aaa ctc acg att atc ccg ccg ggc aag cct       48
```

```
Met Met Met Asp Arg Ala Lys Leu Thr Ile Ile Pro Pro Gly Lys Pro
 1               5                  10                 15 ttg acc gga cgc gcc atg ccg ccg gga tcg aag tcg atc acc aac cgc      96
Leu Thr Gly Arg Ala Met Pro Pro Gly Ser Lys Ser Ile Thr Asn Arg
             20                  25                  30 gca ttg ctg ctc gcc ggc ctc gcc aag ggc acg agc cgg tta act ggt     144
Ala Leu Leu Leu Ala Gly Leu Ala Lys Gly Thr Ser Arg Leu Thr Gly
         35                  40                  45 gcg ctg aag agc gac gat acc cgc tat atg gcc gaa gcg ctg cgt gcg     192
Ala Leu Lys Ser Asp Asp Thr Arg Tyr Met Ala Glu Ala Leu Arg Ala
     50                  55                  60 atg ggt gta acg atc gac gag ccc gac gac acc acg ttc atc gtc aaa     240
Met Gly Val Thr Ile Asp Glu Pro Asp Asp Thr Thr Phe Ile Val Lys
 65                  70                  75                  80 ggc agc ggc aag ctg cag ctg ccg gta gcc ccg ctt ttc ctc ggc aat     288
Gly Ser Gly Lys Leu Gln Leu Pro Val Ala Pro Leu Phe Leu Gly Asn
                 85                  90                  95 gcc ggc acg gca acg cgc ttc ctg acg gcg gcc gca ctg gtg gac         336
Ala Gly Thr Ala Thr Arg Phe Leu Thr Ala Ala Ala Leu Val Asp
             100                 105                 110 ggc aag gtc atc gtc gac ggc gat gcc cat atg cgc aag cgg ccg atc     384
Gly Lys Val Ile Val Asp Gly Asp Ala His Met Arg Lys Arg Pro Ile
             115                 120                 125 gga ccg cta gtc gac gcg ttg cgc tcg ctc ggc atc gat gcc tcg gct     432
Gly Pro Leu Val Asp Ala Leu Arg Ser Leu Gly Ile Asp Ala Ser Ala
         130                 135                 140 gaa act ggc tgc ccg cca gtc acg atc aac ggc acc ggc cgc ttc gag     480
Glu Thr Gly Cys Pro Pro Val Thr Ile Asn Gly Thr Gly Arg Phe Glu
145                 150                 155                 160 gca agc cgc gtg cag atc gat ggc ggc ctg tcc agc cag tat gtc tcg     528
Ala Ser Arg Val Gln Ile Asp Gly Gly Leu Ser Ser Gln Tyr Val Ser
                 165                 170                 175 gcg ctc ctg atg atg gcc gcc ggc ggc gat cgc act gtc gat gtc gag     576
Ala Leu Leu Met Met Ala Ala Gly Gly Asp Arg Thr Val Asp Val Glu
             180                 185                 190 ctt ctc ggc gaa cat atc ggc gct ctc ggc tat atc gac ctg acc gtt     624
Leu Leu Gly Glu His Ile Gly Ala Leu Gly Tyr Ile Asp Leu Thr Val
             195                 200                 205 gcc gcc atg cgc gct ttc ggc gcg aag gtt gag cgt gtg agc ccg gtc     672
Ala Ala Met Arg Ala Phe Gly Ala Lys Val Glu Arg Val Ser Pro Val
         210                 215                 220 gcc tgg cgc gtc gag ccc acc ggc tat cat gcg gcc gac ttc gcg atc     720
Ala Trp Arg Val Glu Pro Thr Gly Tyr His Ala Ala Asp Phe Ala Ile
225                 230                 235                 240 gag ccg gat gcc tct gct gcg acc tat ctc tgg gcc gcc gaa gtt ctg     768
Glu Pro Asp Ala Ser Ala Ala Thr Tyr Leu Trp Ala Ala Glu Val Leu
                 245                 250                 255 agc ggc ggc aag atc gat ctc ggc acg ccg gcg gaa cag ttc tcg caa     816
Ser Gly Gly Lys Ile Asp Leu Gly Thr Pro Ala Glu Gln Phe Ser Gln
             260                 265                 270 ccg gat gcg aaa gcc tat gat ctg att tct aaa ttc ccg cat ctg cct     864
Pro Asp Ala Lys Ala Tyr Asp Leu Ile Ser Lys Phe Pro His Leu Pro
         275                 280                 285 gct gtc atc gac ggc tcg cag atg cag gac gcc atc ccg acg ctc gcc     912
Ala Val Ile Asp Gly Ser Gln Met Gln Asp Ala Ile Pro Thr Leu Ala
     290                 295                 300 gtt ctc gcc gca ttc aac gaa atg cct gtg cgc ttc gtc ggt atc gaa     960
Val Leu Ala Ala Phe Asn Glu Met Pro Val Arg Phe Val Gly Ile Glu
305                 310                 315                 320
```

```
aac ctg cgc gtc aag gaa tgc gat cgt atc cgc gcg ctc tcg agc ggc      1008
Asn Leu Arg Val Lys Glu Cys Asp Arg Ile Arg Ala Leu Ser Ser Gly
            325                 330                 335 cta tcc cgc atc gtt ccg aac ctc ggc acg gaa gag ggc gac gat ctc      1056
Leu Ser Arg Ile Val Pro Asn Leu Gly Thr Glu Glu Gly Asp Asp Leu
        340                 345                 350 atc atc gcc tcc gat ccg agc ctt gcc ggc aaa atc ctg acc gca gag      1104
Ile Ile Ala Ser Asp Pro Ser Leu Ala Gly Lys Ile Leu Thr Ala Glu
    355                 360                 365 atc gat agc ttt gcc gat cac cgc atc gcc atg agc ttt gtg ctg gcc      1152
Ile Asp Ser Phe Ala Asp His Arg Ile Ala Met Ser Phe Val Leu Ala
370                 375                 380 ggc ctg aag atc ggc ggc att acc att ctc gac ccc gac tgc gtc gcc      1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc      1248
Lys Thr Phe Pro Ser Tyr Trp Asn Val Leu Ser Ser Leu Gly Val Ala
                405                 410                 415 tac gaa gac tga                                                      1260
Tyr Glu Asp <210> SEQ ID NO 15
<211> LENGTH: 419
<212> TYPE: PRT
<213> ORGANISM: Brevundomonas vesicularis
<220> FEATURE:
<221> NAME/KEY: VARIANT
<222> LOCATION: (0)...(0)
<223> OTHER INFORMATION: GRG8m6

<400> SEQUENCE: 15

Met Met Met Asp Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Asp Thr Thr Phe Ile Val Lys
65                  70                  75                  80

Gly Ser Gly Lys Leu Gln Leu Pro Val Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Asp Ala Leu Arg Ser Leu Gly Ile Asp Ala Ser Ala
    130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Thr Val Asp Val Glu
            180                 185                 190

Leu Leu Gly Glu His Ile Gly Ala Leu Gly Tyr Ile Asp Leu Thr Val
        195                 200                 205

Ala Ala Met Arg Ala Phe Gly Ala Lys Val Glu Arg Val Ser Pro Val
```

```
                210                 215                 220
Ala Trp Arg Val Glu Pro Thr Gly Tyr His Ala Asp Phe Ala Ile
225                 230                 235                 240

Glu Pro Asp Ala Ser Ala Thr Tyr Leu Trp Ala Ala Glu Val Leu
                245                 250                 255

Ser Gly Gly Lys Ile Asp Leu Gly Thr Pro Ala Glu Gln Phe Ser Gln
                260                 265                 270

Pro Asp Ala Lys Ala Tyr Asp Leu Ile Ser Lys Phe Pro His Leu Pro
                275                 280                 285

Ala Val Ile Asp Gly Ser Gln Met Gln Asp Ala Ile Pro Thr Leu Ala
                290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Glu Gly Asp Asp Leu
                340                 345                 350

Ile Ile Ala Ser Asp Pro Ser Leu Ala Gly Lys Ile Leu Thr Ala Glu
                355                 360                 365

Ile Asp Ser Phe Ala Asp His Arg Ile Ala Met Ser Phe Val Leu Ala
                370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
                405                 410                 415

Tyr Glu Asp

<210> SEQ ID NO 16
<211> LENGTH: 1260
<212> TYPE: DNA
<213> ORGANISM: Brevundomonas vesicularis
<220> FEATURE:
<221> NAME/KEY: CDS
<222> LOCATION: (1)...(1257)
<223> OTHER INFORMATION: grg8m7

<400> SEQUENCE: 16 atg atg atg ggt aga gcc aaa ctc acg att atc ccg ccg ggc aag cct    48
Met Met Met Gly Arg Ala Lys Leu Thr Ile Ile Pro Pro Gly Lys Pro
 1               5                  10                  15 ttg acc gga cgc gcc atg ccg ccg gga tcg aag tcg atc acc aac cgc    96
Leu Thr Gly Arg Ala Met Pro Pro Gly Ser Lys Ser Ile Thr Asn Arg
             20                  25                  30 gca ttg ctg ctc gcc ggc ctc gcc aag ggc acg agc cgg cta acc ggt   144
Ala Leu Leu Leu Ala Gly Leu Ala Lys Gly Thr Ser Arg Leu Thr Gly
         35                  40                  45 gcg ctg aag agc gac gat acc cgc tat atg gcc gaa gcg ctg cgt gcg   192
Ala Leu Lys Ser Asp Asp Thr Arg Tyr Met Ala Glu Ala Leu Arg Ala
     50                  55                  60 atg ggt gta acg atc gac gag ccc gac gac acc acg ttc atc gtc aaa   240
Met Gly Val Thr Ile Asp Glu Pro Asp Asp Thr Thr Phe Ile Val Lys
 65                  70                  75                  80 ggc agc ggc aaa ctg cag ccg ccg gca gcc ccg ctt ttc ctc ggc aat   288
Gly Ser Gly Lys Leu Gln Pro Pro Ala Ala Pro Leu Phe Leu Gly Asn
                 85                  90                  95 gcc ggc acg gca acg cgc ttc ctg acg gcg gcc gcg gca ctg gtg gac   336
Ala Gly Thr Ala Thr Arg Phe Leu Thr Ala Ala Ala Ala Leu Val Asp
            100                 105                 110
```

```
ggt aag atc atc gtc gac ggc gat gcc cat atg cgc aag cgg ctg atc        384
Gly Lys Ile Ile Val Asp Gly Asp Ala His Met Arg Lys Arg Leu Ile
        115                 120                 125 gga ccg cta gtc gac gcg ttg cgc tcg ctc ggc atc gat gcc tcg gct        432
Gly Pro Leu Val Asp Ala Leu Arg Ser Leu Gly Ile Asp Ala Ser Ala
130                 135                 140 gaa acc ggc tgc ccg cca gtc acg atc aac ggc acc ggc cgc ttc gag        480
Glu Thr Gly Cys Pro Pro Val Thr Ile Asn Gly Thr Gly Arg Phe Glu
145                 150                 155                 160 gca agc cgc gtg cag atc gat ggc ggc ctg tcc agc cag tat gtc tcg        528
Ala Ser Arg Val Gln Ile Asp Gly Gly Leu Ser Ser Gln Tyr Val Ser
                165                 170                 175 gcg ctc ctg atg atg gcc gcc ggc ggt gat cgc gct gtc gat gtc gag        576
Ala Leu Leu Met Met Ala Ala Gly Gly Asp Arg Ala Val Asp Val Glu
        180                 185                 190 ctt ctc ggc gaa cat atc ggc gct ctc ggc tat atc gac ctg acc gtt        624
Leu Leu Gly Glu His Ile Gly Ala Leu Gly Tyr Ile Asp Leu Thr Val
        195                 200                 205 gcc gcc atg cgc gct ttc ggc gcg aag gtt gag cgt gtg agc ccg gtc        672
Ala Ala Met Arg Ala Phe Gly Ala Lys Val Glu Arg Val Ser Pro Val
210                 215                 220 gcc tgg cgc gtc gag ccc acc ggc tat cat gcg gcc gac ttc gtg atc        720
Ala Trp Arg Val Glu Pro Thr Gly Tyr His Ala Ala Asp Phe Val Ile
225                 230                 235                 240 gag ccg gat gcc tct gct gcg acc tat ctc tgg gcc gcc gaa gtt ctg        768
Glu Pro Asp Ala Ser Ala Ala Thr Tyr Leu Trp Ala Ala Glu Val Leu
                245                 250                 255 agc ggc ggc aag atc gat ctc ggc acg ccg gcg gaa cag ttc tcg caa        816
Ser Gly Gly Lys Ile Asp Leu Gly Thr Pro Ala Glu Gln Phe Ser Gln
        260                 265                 270 ccg gat gcg aaa gcc tat gat ctg att tcg aaa tac ccg cat ctg cct        864
Pro Asp Ala Lys Ala Tyr Asp Leu Ile Ser Lys Tyr Pro His Leu Pro
        275                 280                 285 gct gtc atc gac ggc tcg cag atg cag gac gcc atc ccg acg atc gcc        912
Ala Val Ile Asp Gly Ser Gln Met Gln Asp Ala Ile Pro Thr Ile Ala
        290                 295                 300 gtt ctc gcc gct ttc aac gaa atg cct gtg cgc ttc gtc ggt atc gaa        960
Val Leu Ala Ala Phe Asn Glu Met Pro Val Arg Phe Val Gly Ile Glu
305                 310                 315                 320 aac ctg cgc gtc aag gaa tgc gat cgt atc cgc gcg ctc tcg agc ggc       1008
Asn Leu Arg Val Lys Glu Cys Asp Arg Ile Arg Ala Leu Ser Ser Gly
                325                 330                 335 cta tcc cgc atc gtt ccg aac ctc ggc acg gaa gag ggc gac gat ctc       1056
Leu Ser Arg Ile Val Pro Asn Leu Gly Thr Glu Glu Gly Asp Asp Leu
        340                 345                 350 atc atc gcc tcc gat ccg agc ctt gcc ggc aaa atc ctg acc gca gag       1104
Ile Ile Ala Ser Asp Pro Ser Leu Ala Gly Lys Ile Leu Thr Ala Glu
        355                 360                 365 atc gat agc ttt gcc gat cac cgc atc gcc atg agc ttt gcg ctg gcc       1152
Ile Asp Ser Phe Ala Asp His Arg Ile Ala Met Ser Phe Ala Leu Ala
        370                 375                 380 ggc ctg aag atc ggc ggc att acc att ctc gac ccc gac tgc gtc gcc       1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc       1248
Lys Thr Phe Pro Ser Tyr Trp Asn Val Leu Ser Ser Leu Gly Val Ala
                405                 410                 415 tac gaa gac tga                                                        1260
Tyr Glu Asp
```

<210> SEQ ID NO 17
<211> LENGTH: 419
<212> TYPE: PRT
<213> ORGANISM: Brevundomonas vesicularis
<220> FEATURE:
<221> NAME/KEY: VARIANT
<222> LOCATION: (0)...(0)
<223> OTHER INFORMATION: GRG8m7

<400> SEQUENCE: 17

```
Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
50                  55                  60

Met Gly Val Thr Ile Asp Glu Pro Asp Asp Thr Thr Phe Ile Val Lys
65                  70                  75                  80

Gly Ser Gly Lys Leu Gln Pro Pro Ala Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Ile Ile Val Asp Gly Asp Ala His Met Arg Lys Arg Leu Ile
        115                 120                 125

Gly Pro Leu Val Asp Ala Leu Arg Ser Leu Gly Ile Asp Ala Ser Ala
    130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
            180                 185                 190

Leu Leu Gly Glu His Ile Gly Ala Leu Gly Tyr Ile Asp Leu Thr Val
        195                 200                 205

Ala Ala Met Arg Ala Phe Gly Ala Lys Val Glu Arg Val Ser Pro Val
    210                 215                 220

Ala Trp Arg Val Glu Pro Thr Gly Tyr His Ala Ala Asp Phe Val Ile
225                 230                 235                 240

Glu Pro Asp Ala Ser Ala Ala Thr Tyr Leu Trp Ala Ala Glu Val Leu
                245                 250                 255

Ser Gly Gly Lys Ile Asp Leu Gly Thr Pro Ala Glu Gln Phe Ser Gln
            260                 265                 270

Pro Asp Ala Lys Ala Tyr Asp Leu Ile Ser Lys Tyr Pro His Leu Pro
        275                 280                 285

Ala Val Ile Asp Gly Ser Gln Met Gln Asp Ala Ile Pro Thr Ile Ala
    290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Glu Gly Asp Asp Leu
            340                 345                 350
```

-continued

```
            Ile Ile Ala Ser Asp Pro Ser Leu Ala Gly Lys Ile Leu Thr Ala Glu
                        355                 360                 365

Ile Asp Ser Phe Ala Asp His Arg Ile Ala Met Ser Phe Ala Leu Ala
                    370                 375                 380

Gly Leu Lys Ile Gly Ile Thr Ile Leu Asp Pro Asp Cys Val Ala
            385                 390                 395                 400

Lys Thr Phe Pro Ser Tyr Trp Asn Val Leu Ser Ser Leu Gly Val Ala
                            405                 410                 415

Tyr Glu Asp

<210> SEQ ID NO 18
            <211> LENGTH: 1260
            <212> TYPE: DNA
            <213> ORGANISM: Brevundomonas vesicularis
            <220> FEATURE:
            <221> NAME/KEY: CDS
            <222> LOCATION: (1)...(1257)
            <223> OTHER INFORMATION: grg8m8

<400> SEQUENCE: 18 atg atg atg ggt aga gcc aaa ctc acg att atc ccg ccg ggc aag cct        48
            Met Met Met Gly Arg Ala Lys Leu Thr Ile Ile Pro Pro Gly Lys Pro
            1               5                   10                  15 ttg acc gga cgc gcc atg ccg ccg gga tcg aag tcg atc acc aac cgc        96
            Leu Thr Gly Arg Ala Met Pro Pro Gly Ser Lys Ser Ile Thr Asn Arg
                            20                  25                  30 gca ttg ctg ctc gcc ggc ctc gcc aag ggc acg agc cgg cta acc ggt       144
            Ala Leu Leu Leu Ala Gly Leu Ala Lys Gly Thr Ser Arg Leu Thr Gly
                        35                  40                  45 gcg ctg aag agc gac gat acc cgc tat atg gcc gaa gcg ctg cgt gcg       192
            Ala Leu Lys Ser Asp Asp Thr Arg Tyr Met Ala Glu Ala Leu Arg Ala
                50                  55                  60 atg gat gta atg atc gac gag ccc gac gac acc acg ttc atc gtc aaa       240
            Met Asp Val Met Ile Asp Glu Pro Asp Asp Thr Thr Phe Ile Val Lys
            65                  70                  75                  80 ggc agc ggc aag ctg cag ccg ccg gca gcc ccg ctt ttc ctc ggc aat       288
            Gly Ser Gly Lys Leu Gln Pro Pro Ala Ala Pro Leu Phe Leu Gly Asn
                            85                  90                  95 gcc ggc acg gca acg cgc ttc ctg acg gcg gcc gcg gca ctg gtg gac       336
            Ala Gly Thr Ala Thr Arg Phe Leu Thr Ala Ala Ala Ala Leu Val Asp
                        100                 105                 110 ggc aag gtc atc gtc gac ggc gat gcc cat atg cgc aag cgg ccg atc       384
            Gly Lys Val Ile Val Asp Gly Asp Ala His Met Arg Lys Arg Pro Ile
                115                 120                 125 gga ccg cta gtc gac gcg ttg cgc tcg ctc ggc atc gat gcc tcg gct       432
            Gly Pro Leu Val Asp Ala Leu Arg Ser Leu Gly Ile Asp Ala Ser Ala
            130                 135                 140 gaa aca ggc tgc ccg cca gtc acg atc aac ggc acc ggc cgc ttc gag       480
            Glu Thr Gly Cys Pro Pro Val Thr Ile Asn Gly Thr Gly Arg Phe Glu
            145                 150                 155                 160 gca agc cgc gtg cag atc gat ggc agc ctg tcc agc cag tat gtc tcg       528
            Ala Ser Arg Val Gln Ile Asp Gly Ser Leu Ser Ser Gln Tyr Val Ser
                            165                 170                 175 gcg ctc ctg atg atg gcc gcc ggc ggt gat cgc gct gtc gat gtc gag       576
            Ala Leu Leu Met Met Ala Ala Gly Gly Asp Arg Ala Val Asp Val Glu
                        180                 185                 190 ctt ctc ggc gaa cat atc ggc gct ctc ggc tat atc gac ctg acc gtt       624
            Leu Leu Gly Glu His Ile Gly Ala Leu Gly Tyr Ile Asp Leu Thr Val
                195                 200                 205 gcc gcc atg cgc gct ttc ggc gcg aag gtt gag cgt gtg agc ccg gtc       672
```

```
                Ala Ala Met Arg Ala Phe Gly Ala Lys Val Glu Arg Val Ser Pro Val
                        210                 215                 220 gcc tgg cgc gtc gag ccc acc ggc tat cat gcg gcc gac tac gtg atc            720
Ala Trp Arg Val Glu Pro Thr Gly Tyr His Ala Ala Asp Tyr Val Ile
225                 230                 235                 240 gag ccg gat gcc tct gct gcg acc tat ctc tgg gcc gcc gaa gtt ctg            768
Glu Pro Asp Ala Ser Ala Ala Thr Tyr Leu Trp Ala Ala Glu Val Leu
                245                 250                 255 agc ggc ggc aag atc gat ctc ggc acg ccg gcg gaa cag ttc tcg caa            816
Ser Gly Gly Lys Ile Asp Leu Gly Thr Pro Ala Glu Gln Phe Ser Gln
            260                 265                 270 ccg gat gcg aaa gcc tat gat ctg att tcg aaa ttc ccg cat ctg cct            864
Pro Asp Ala Lys Ala Tyr Asp Leu Ile Ser Lys Phe Pro His Leu Pro
        275                 280                 285 gct gtc atc gac ggc tcg cag atg cag gac gcc atc ccg acg ctc gcc            912
Ala Val Ile Asp Gly Ser Gln Met Gln Asp Ala Ile Pro Thr Leu Ala
    290                 295                 300 gtt ctc gcc gct ttc aac gaa atg cct gtg cgc ttc gcc ggt atc gaa            960
Val Leu Ala Ala Phe Asn Glu Met Pro Val Arg Phe Ala Gly Ile Glu
305                 310                 315                 320 aac ctg cgc ctc aag gaa tgc gat cgt atc cgc gcg ctc tcg aac ggc           1008
Asn Leu Arg Leu Lys Glu Cys Asp Arg Ile Arg Ala Leu Ser Asn Gly
                325                 330                 335 cta tcc cgc atc gtt ccg aac ctc ggc acg gaa gag ggc gac gat ctc           1056
Leu Ser Arg Ile Val Pro Asn Leu Gly Thr Glu Glu Gly Asp Asp Leu
                340                 345                 350 atc atc gcc tcc gat ccg agc ctt gcc ggc aaa atc ctg acc gca gag           1104
Ile Ile Ala Ser Asp Pro Ser Leu Ala Gly Lys Ile Leu Thr Ala Glu
            355                 360                 365 atc gat agc ttt gcc gat cac cgc atc gcc atg agc ttt gcg ctg gcc           1152
Ile Asp Ser Phe Ala Asp His Arg Ile Ala Met Ser Phe Ala Leu Ala
        370                 375                 380 ggc ctg aag atc ggc ggc att acc att ctc gac ccc gac tgc gtc gcc           1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc           1248
Lys Thr Phe Pro Ser Tyr Trp Asn Val Leu Ser Ser Leu Gly Val Ala
                405                 410                 415 tac gaa gac tga                                                            1260
Tyr Glu Asp <210> SEQ ID NO 19
<211> LENGTH: 419
<212> TYPE: PRT
<213> ORGANISM: Brevundomonas vesicularis
<220> FEATURE:
<221> NAME/KEY: VARIANT
<222> LOCATION: (0)...(0)
<223> OTHER INFORMATION: GRG8m8

<400> SEQUENCE: 19

Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
                20                  25                  30

Ala Leu Leu Leu Ala Gly Leu Ala Lys Gly Thr Ser Arg Leu Thr Gly
            35                  40                  45

Ala Leu Lys Ser Asp Asp Thr Arg Tyr Met Ala Glu Ala Leu Arg Ala
        50                  55                  60

Met Asp Val Met Ile Asp Glu Pro Asp Asp Thr Thr Phe Ile Val Lys
```

```
            65                  70                  75                  80
Gly Ser Gly Lys Leu Gln Pro Ala Ala Pro Leu Phe Leu Gly Asn
                85                  90                  95
Ala Gly Thr Ala Thr Arg Phe Leu Thr Ala Ala Ala Leu Val Asp
            100                 105                 110
Gly Lys Val Ile Val Asp Gly Asp Ala His Met Arg Lys Arg Pro Ile
            115                 120                 125
Gly Pro Leu Val Asp Ala Leu Arg Ser Leu Gly Ile Asp Ala Ser Ala
        130                 135                 140
Glu Thr Gly Cys Pro Pro Val Thr Ile Asn Gly Thr Gly Arg Phe Glu
145                 150                 155                 160
Ala Ser Arg Val Gln Ile Asp Gly Ser Leu Ser Ser Gln Tyr Val Ser
                165                 170                 175
Ala Leu Leu Met Met Ala Ala Gly Gly Asp Arg Ala Val Asp Val Glu
            180                 185                 190
Leu Leu Gly Glu His Ile Gly Ala Leu Gly Tyr Ile Asp Leu Thr Val
        195                 200                 205
Ala Ala Met Arg Ala Phe Gly Ala Lys Val Glu Arg Val Ser Pro Val
    210                 215                 220
Ala Trp Arg Val Glu Pro Thr Gly Tyr His Ala Ala Asp Tyr Val Ile
225                 230                 235                 240
Glu Pro Asp Ala Ser Ala Ala Thr Tyr Leu Trp Ala Ala Glu Val Leu
                245                 250                 255
Ser Gly Gly Lys Ile Asp Leu Gly Thr Pro Ala Glu Gln Phe Ser Gln
            260                 265                 270
Pro Asp Ala Lys Ala Tyr Asp Leu Ile Ser Lys Phe Pro His Leu Pro
        275                 280                 285
Ala Val Ile Asp Gly Ser Gln Met Gln Asp Ala Ile Pro Thr Leu Ala
    290                 295                 300
Val Leu Ala Ala Phe Asn Glu Met Pro Val Arg Phe Ala Gly Ile Glu
305                 310                 315                 320
Asn Leu Arg Leu Lys Glu Cys Asp Arg Ile Arg Ala Leu Ser Asn Gly
                325                 330                 335
Leu Ser Arg Ile Val Pro Asn Leu Gly Thr Glu Glu Gly Asp Asp Leu
            340                 345                 350
Ile Ile Ala Ser Asp Pro Ser Leu Ala Gly Lys Ile Leu Thr Ala Glu
        355                 360                 365
Ile Asp Ser Phe Ala Asp His Arg Ile Ala Met Ser Phe Ala Leu Ala
    370                 375                 380
Gly Leu Lys Ile Gly Gly Ile Thr Ile Leu Asp Pro Asp Cys Val Ala
385                 390                 395                 400
Lys Thr Phe Pro Ser Tyr Trp Asn Val Leu Ser Ser Leu Gly Val Ala
                405                 410                 415
Tyr Glu Asp

<210> SEQ ID NO 20
<211> LENGTH: 1260
<212> TYPE: DNA
<213> ORGANISM: Brevundomonas vesicularis
<220> FEATURE:
<221> NAME/KEY: CDS
<222> LOCATION: (1)...(1257)
<223> OTHER INFORMATION: grg8m9

<400> SEQUENCE: 20
```

-continued

| | |
|---|---|
| atg atg atg ggt aga gcc aaa ctc acg att atc ccg ccg ggc aag cct<br>Met Met Met Gly Arg Ala Lys Leu Thr Ile Ile Pro Pro Gly Lys Pro<br>1                          5                      10                    15 | 48 |
| ttg acc gga cgc gcc atg ccg ccg gga tcg aag tcg atc acc aac cgc<br>Leu Thr Gly Arg Ala Met Pro Pro Gly Ser Lys Ser Ile Thr Asn Arg<br>                    20                      25                      30 | 96 |
| gca ttg ctg ctc gcc ggc ctc gcc aag ggc acg agc cgg cta acc ggt<br>Ala Leu Leu Leu Ala Gly Leu Ala Lys Gly Thr Ser Arg Leu Thr Gly<br>      35                    40                      45 | 144 |
| gcg ctg aag agc gac gat acc cgc tat atg gcc gaa gcg ctg cgt gcg<br>Ala Leu Lys Ser Asp Asp Thr Arg Tyr Met Ala Glu Ala Leu Arg Ala<br>50                        55                      60 | 192 |
| atg ggt gta acg atc gac gag ccc gac gac acc acg ttc atc gtc aaa<br>Met Gly Val Thr Ile Asp Glu Pro Asp Asp Thr Thr Phe Ile Val Lys<br>65                        70                      75                    80 | 240 |
| ggc agc ggc aag ctg cag ccg ccg gca gcc ccg ctt ttc ctc ggc aat<br>Gly Ser Gly Lys Leu Gln Pro Pro Ala Ala Pro Leu Phe Leu Gly Asn<br>                    85                    90                      95 | 288 |
| gcc ggc acg gca acg cgc ttc ctg acg gcg gcc gca ctg gtg gac<br>Ala Gly Thr Ala Thr Arg Phe Leu Thr Ala Ala Ala Leu Val Asp<br>                    100                  105                  110 | 336 |
| ggc aag gtc atc gtc gac ggc gat gcc cat atg cgc aag cgg ccg atc<br>Gly Lys Val Ile Val Asp Gly Asp Ala His Met Arg Lys Arg Pro Ile<br>          115                    120                  125 | 384 |
| gga ccg cta gtc gac gcg ttg cgc tcg ctc ggc atc gat gcc tcg gct<br>Gly Pro Leu Val Asp Ala Leu Arg Ser Leu Gly Ile Asp Ala Ser Ala<br>130                       135                  140 | 432 |
| gaa acc ggc tgc ccg cca gtc acg atc aac ggc acc ggc cgc ttc gag<br>Glu Thr Gly Cys Pro Pro Val Thr Ile Asn Gly Thr Gly Arg Phe Glu<br>145                      150                    155                  160 | 480 |
| gca agc cgc gtg cag atc gat ggc ggc ctg tcc agc cag tat gtc tcg<br>Ala Ser Arg Val Gln Ile Asp Gly Gly Leu Ser Ser Gln Tyr Val Ser<br>                    165                  170                  175 | 528 |
| gcg ctc ctg atg atg gcc gcc ggc ggc gat cgc gct gtc gat gtc gag<br>Ala Leu Leu Met Met Ala Ala Gly Gly Asp Arg Ala Val Asp Val Glu<br>                180                  185                  190 | 576 |
| ctt ttc ggc gaa cat atc ggc gct ctc ggc tat atc gac ctg acc gtt<br>Leu Phe Gly Glu His Ile Gly Ala Leu Gly Tyr Ile Asp Leu Thr Val<br>          195                    200                  205 | 624 |
| gcc gcc atg cgc gct ttc ggc gcg aag gtt gag cgt gtg agc ccg gtc<br>Ala Ala Met Arg Ala Phe Gly Ala Lys Val Glu Arg Val Ser Pro Val<br>210                      215                  220 | 672 |
| gcc tgg cgc gtc gag ccc acc ggc tat cat gcg gcc gac ttc gtg atc<br>Ala Trp Arg Val Glu Pro Thr Gly Tyr His Ala Ala Asp Phe Val Ile<br>225                      230                    235                  240 | 720 |
| gag ccg gat gcc tct gct gcg acc tat ctc tgg gcc gcc gaa gtt ctg<br>Glu Pro Asp Ala Ser Ala Ala Thr Tyr Leu Trp Ala Ala Glu Val Leu<br>                    245                  250                  255 | 768 |
| agc ggc ggc aag atc gat ctc ggc acg ccg gcg gaa cag ttc tcg caa<br>Ser Gly Gly Lys Ile Asp Leu Gly Thr Pro Ala Glu Gln Phe Ser Gln<br>                260                    265                  270 | 816 |
| ccg gat gcg aaa gcc tat gat ctg att tcg aaa ttc ccg cat ctg cct<br>Pro Asp Ala Lys Ala Tyr Asp Leu Ile Ser Lys Phe Pro His Leu Pro<br>          275                    280                  285 | 864 |
| gct gtc atc gac ggc tcg cag atg cag gac gcc atc ccg acg ctc gcc<br>Ala Val Ile Asp Gly Ser Gln Met Gln Asp Ala Ile Pro Thr Leu Ala<br>290                       295                    300 | 912 |
| gtt ctc gcc gct ttc aac gaa atg cct gtg cgc ttc gtc ggt atc gaa<br>Val Leu Ala Ala Phe Asn Glu Met Pro Val Arg Phe Val Gly Ile Glu<br>305                      310                    315                  320 | 960 |

```
aac ctg cgc gtc aag gaa tgc gat cgt atc cgc gcg ctc tcg agc ggc    1008
Asn Leu Arg Val Lys Glu Cys Asp Arg Ile Arg Ala Leu Ser Ser Gly
            325                 330                 335 cta tcc cgc atc gtt ccg aac ctc ggc acg gaa gag ggc gac gat ctc    1056
Leu Ser Arg Ile Val Pro Asn Leu Gly Thr Glu Glu Gly Asp Asp Leu
        340                 345                 350 atc atc gcc tcc gat ccg agc ctt gcc ggc aaa atc ctg acc gca gag    1104
Ile Ile Ala Ser Asp Pro Ser Leu Ala Gly Lys Ile Leu Thr Ala Glu
                355                 360                 365 atc gat agc ttt gcc gat cac cgc atc gcc atg agc ttt gcg ctg gcc    1152
Ile Asp Ser Phe Ala Asp His Arg Ile Ala Met Ser Phe Ala Leu Ala
    370                 375                 380 ggc ctg aag atc ggc ggc att acc att ctc gac ccc gac tgc gtc gcc    1200
Gly Leu Lys Ile Gly Gly Ile Thr Ile Leu Asp Pro Asp Cys Val Ala
385                 390                 395                 400 aag aca ttc ccg tcc tac tgg aat gtg ctg tct tcg ctg ggg gtc gcc    1248
Lys Thr Phe Pro Ser Tyr Trp Asn Val Leu Ser Ser Leu Gly Val Ala
                405                 410                 415 tac gaa gac tga                                                    1260
Tyr Glu Asp <210> SEQ ID NO 21
<211> LENGTH: 419
<212> TYPE: PRT
<213> ORGANISM: Brevundomonas vesicularis
<220> FEATURE:
<221> NAME/KEY: VARIANT
<222> LOCATION: (0)...(0)
<223> OTHER INFORMATION: GRG8m9

<400> SEQUENCE: 21

Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Thr Thr Phe Ile Val Lys
65                  70                  75                  80

Gly Ser Gly Lys Leu Gln Pro Pro Ala Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Asp Ala Leu Arg Ser Leu Gly Ile Asp Ala Ser Ala
    130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
            180                 185                 190

Leu Phe Gly Glu His Ile Gly Ala Leu Gly Tyr Ile Asp Leu Thr Val
        195                 200                 205
```

```
Ala Ala Met Arg Ala Phe Gly Ala Lys Val Glu Arg Val Ser Pro Val
    210                 215                 220
Ala Trp Arg Val Glu Pro Thr Gly Tyr His Ala Ala Asp Phe Val Ile
225                 230                 235                 240
Glu Pro Asp Ala Ser Ala Ala Thr Tyr Leu Trp Ala Ala Glu Val Leu
                245                 250                 255
Ser Gly Gly Lys Ile Asp Leu Gly Thr Pro Ala Glu Gln Phe Ser Gln
            260                 265                 270
Pro Asp Ala Lys Ala Tyr Asp Leu Ile Ser Lys Phe Pro His Leu Pro
        275                 280                 285
Ala Val Ile Asp Gly Ser Gln Met Gln Asp Ala Ile Pro Thr Leu Ala
    290                 295                 300
Val Leu Ala Ala Phe Asn Glu Met Pro Val Arg Phe Val Gly Ile Glu
305                 310                 315                 320
Asn Leu Arg Val Lys Glu Cys Asp Arg Ile Arg Ala Leu Ser Ser Gly
                325                 330                 335
Leu Ser Arg Ile Val Pro Asn Leu Gly Thr Glu Gly Asp Asp Leu
            340                 345                 350
Ile Ile Ala Ser Asp Pro Ser Leu Ala Gly Lys Ile Leu Thr Ala Glu
        355                 360                 365
Ile Asp Ser Phe Ala Asp His Arg Ile Ala Met Ser Phe Ala Leu Ala
    370                 375                 380
Gly Leu Lys Ile Gly Gly Ile Thr Ile Leu Asp Pro Asp Cys Val Ala
385                 390                 395                 400
Lys Thr Phe Pro Ser Tyr Trp Asn Val Leu Ser Ser Leu Gly Val Ala
                405                 410                 415
Tyr Glu Asp

<210> SEQ ID NO 22
<211> LENGTH: 1260
<212> TYPE: DNA
<213> ORGANISM: Brevundomonas vesicularis
<220> FEATURE:
<221> NAME/KEY: CDS
<222> LOCATION: (1)...(1257)
<223> OTHER INFORMATION: grg8m10

<400> SEQUENCE: 22 atg atg atg ggt aga gcc aaa ctc acg att atc ccg ccg ggc aag cct      48
Met Met Met Gly Arg Ala Lys Leu Thr Ile Ile Pro Pro Gly Lys Pro
1               5                   10                  15 ttg acc gga cgc gcc atg ccg ccg gga tcg aag tcg atc acc aac cgc      96
Leu Thr Gly Arg Ala Met Pro Pro Gly Ser Lys Ser Ile Thr Asn Arg
            20                  25                  30 gca ttg ctg ctc gcc ggc ctc gcc aag ggc acg agc cgg cta acc ggt     144
Ala Leu Leu Leu Ala Gly Leu Ala Lys Gly Thr Ser Arg Leu Thr Gly
        35                  40                  45 gcg ctg aag agc gac gat acc cgc tat atg gcc gaa gcg ctg cgt gcg     192
Ala Leu Lys Ser Asp Asp Thr Arg Tyr Met Ala Glu Ala Leu Arg Ala
    50                  55                  60 atg ggt gta acg atc gac gag ccc gac gac acc acg ttc atc gtc aaa     240
Met Gly Val Thr Ile Asp Glu Pro Asp Asp Thr Thr Phe Ile Val Lys
65                  70                  75                  80 ggc agc ggc aag ctg gag ccg ccg gca gcc ccg ctt ttc ctc ggc aat     288
Gly Ser Gly Lys Leu Glu Pro Pro Ala Ala Pro Leu Phe Leu Gly Asn
                85                  90                  95 gcc ggc acg gca acg cgc ttc ctg acg gcg gcc gcg gca ctg gtg gac     336
Ala Gly Thr Ala Thr Arg Phe Leu Thr Ala Ala Ala Ala Leu Val Asp
```

-continued

|  |  |  |  |
|---|---|---|---|
| ggc aag gtc atc gtc gac ggc gat gcc cat atg cgc aag cgg ccg atc<br>Gly Lys Val Ile Val Asp Gly Asp Ala His Met Arg Lys Arg Pro Ile<br>115                    120                   125 | 384 |
| gga ccg cta gtc gac gcg ttg cgc tcg ctc ggc atc gat gcc tcg gct<br>Gly Pro Leu Val Asp Ala Leu Arg Ser Leu Gly Ile Asp Ala Ser Ala<br>130                    135                   140 | 432 |
| gaa acc ggc tgc ccg cca gtc acg atc aac ggc acc tgc cgc ttc gag<br>Glu Thr Gly Cys Pro Pro Val Thr Ile Asn Gly Thr Cys Arg Phe Glu<br>145                    150                   155                   160 | 480 |
| gca agc cgc gtg cag atc gat ggc ggc ctg tcc agc cag tat gtc tca<br>Ala Ser Arg Val Gln Ile Asp Gly Gly Leu Ser Ser Gln Tyr Val Ser<br>                 165                   170                   175 | 528 |
| gcg ctc ctg atg atg gcc gcc ggc ggc gat cgc gct gtc gat gtc gag<br>Ala Leu Leu Met Met Ala Ala Gly Gly Asp Arg Ala Val Asp Val Glu<br>            180                   185                   190 | 576 |
| ctt ctc ggc gaa cat atc ggc gct ctc ggc tat atc gac ctg acc gtt<br>Leu Leu Gly Glu His Ile Gly Ala Leu Gly Tyr Ile Asp Leu Thr Val<br>                 195                   200                   205 | 624 |
| gcc gcc atg cgc gct ttc ggc gcg aag gtt gag cgt atg agc ccg gtc<br>Ala Ala Met Arg Ala Phe Gly Ala Lys Val Glu Arg Met Ser Pro Val<br>            210                   215                   220 | 672 |
| gcc tgg cgc gtc gag ccc acc ggc tat cat gcg gcc gac ttc gtg atc<br>Ala Trp Arg Val Glu Pro Thr Gly Tyr His Ala Ala Asp Phe Val Ile<br>225                    230                   235                   240 | 720 |
| gag cct gat gcc tct gct gcg acc tat ctc tgg gcc gcc gaa gtt ctg<br>Glu Pro Asp Ala Ser Ala Ala Thr Tyr Leu Trp Ala Ala Glu Val Leu<br>                     245                   250                   255 | 768 |
| agc ggc ggc acg atc gat ctc ggc acg ccg gcg gaa cag ttc tcg caa<br>Ser Gly Gly Thr Ile Asp Leu Gly Thr Pro Ala Glu Gln Phe Ser Gln<br>                260                   265                   270 | 816 |
| ccg gat gcg aaa gcc tat gat ctg att tcg aaa ttc ccg cat ctg cct<br>Pro Asp Ala Lys Ala Tyr Asp Leu Ile Ser Lys Phe Pro His Leu Pro<br>           275                   280                   285 | 864 |
| gct gtc atc gac ggc tcg cag atg cag gac gcc atc ccg acg ctc gcc<br>Ala Val Ile Asp Gly Ser Gln Met Gln Asp Ala Ile Pro Thr Leu Ala<br>290                    295                   300 | 912 |
| gtt ctc gcc gct ttc aac gaa atg cct gtg cgc ttc gtc ggt atc gaa<br>Val Leu Ala Ala Phe Asn Glu Met Pro Val Arg Phe Val Gly Ile Glu<br>305                    310                   315                   320 | 960 |
| aac ctg cgc gtc aag gaa tgc gat cgt atc cgc gcg ctc tcg agc ggc<br>Asn Leu Arg Val Lys Glu Cys Asp Arg Ile Arg Ala Leu Ser Ser Gly<br>                 325                   330                   335 | 1008 |
| cta tcc cgc atc gtt ccg aac ctc ggc acg gaa gag ggc gac gat ctc<br>Leu Ser Arg Ile Val Pro Asn Leu Gly Thr Glu Glu Gly Asp Asp Leu<br>            340                   345                   350 | 1056 |
| atc atc gcc tcc gat ccg agc ctt gcc ggc aaa atc ctg acc gca gag<br>Ile Ile Ala Ser Asp Pro Ser Leu Ala Gly Lys Ile Leu Thr Ala Glu<br>355                    360                   365 | 1104 |
| atc gat agc ttt gcc gat cac cgc atc gcc atg agc ttt gcg ctg gcc<br>Ile Asp Ser Phe Ala Asp His Arg Ile Ala Met Ser Phe Ala Leu Ala<br>           370                   375                   380 | 1152 |
| ggc ctg aag atc ggc ggc att acc att ctc gac cct gac tgc gtc gcc<br>Gly Leu Lys Ile Gly Gly Ile Thr Ile Leu Asp Pro Asp Cys Val Ala<br>385                    390                   395                   400 | 1200 |
| aag aca ttc ccg tct tac tgg aat gtg ctg tct tcg ctg ggg gtc gcc<br>Lys Thr Phe Pro Ser Tyr Trp Asn Val Leu Ser Ser Leu Gly Val Ala<br>           405                   410                   415 | 1248 |
| tac gaa gac tga | 1260 |

Tyr Glu Asp

<210> SEQ ID NO 23
<211> LENGTH: 419
<212> TYPE: PRT
<213> ORGANISM: Brevundomonas vesicularis
<220> FEATURE:
<221> NAME/KEY: VARIANT
<222> LOCATION: (0)...(0)
<223> OTHER INFORMATION: GRG8m10

<400> SEQUENCE: 23

Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Asp Thr Thr Phe Ile Val Lys
65                  70                  75                  80

Gly Ser Gly Lys Leu Glu Pro Pro Ala Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Asp Ala Leu Arg Ser Leu Gly Ile Asp Ala Ser Ala
    130                 135                 140

Glu Thr Gly Cys Pro Pro Val Thr Ile Asn Gly Thr Cys Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
            180                 185                 190

Leu Leu Gly Glu His Ile Gly Ala Leu Gly Tyr Ile Asp Leu Thr Val
        195                 200                 205

Ala Ala Met Arg Ala Phe Gly Ala Lys Val Glu Arg Met Ser Pro Val
    210                 215                 220

Ala Trp Arg Val Glu Pro Thr Gly Tyr His Ala Ala Asp Phe Val Ile
225                 230                 235                 240

Glu Pro Asp Ala Ser Ala Ala Thr Tyr Leu Trp Ala Ala Glu Val Leu
                245                 250                 255

Ser Gly Gly Thr Ile Asp Leu Gly Thr Pro Ala Glu Gln Phe Ser Gln
            260                 265                 270

Pro Asp Ala Lys Ala Tyr Asp Leu Ile Ser Lys Phe Pro His Leu Pro
        275                 280                 285

Ala Val Ile Asp Gly Ser Gln Met Gln Asp Ala Ile Pro Thr Leu Ala
    290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Glu Gly Asp Asp Leu
            340                 345                 350

```
Ile Ile Ala Ser Asp Pro Ser Leu Ala Gly Lys Ile Leu Thr Ala Glu
        355                 360                 365

Ile Asp Ser Phe Ala Asp His Arg Ile Ala Met Ser Phe Ala Leu Ala
    370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
                405                 410                 415

Tyr Glu Asp
```

GENES CONFERRING HERBICIDE RESISTANCE

CROSS REFERENCE TO RELATED APPLICATION

This application claims the benefit of U.S. Provisional Application Ser. No. 60/640,195, filed Dec. 29, 2004, the contents of which are herein incorporated by reference in their entirety.

FIELD OF THE INVENTION

This invention provides a novel gene encoding a 5-enolpyruvylshikimate-3-phosphate (EPSP) synthase that provides herbicide resistance, and variants thereof. This gene and its variants are useful in plant biology, crop breeding, and plant cell culture.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid to 5-enolpyruvyl-3-phosphoshikimic acid. Inhibition of this enzyme (5-enolpyruvylshikimate-3-phosphate synthase; referred to herein as "EPSP synthase") kills plant cells by shutting down the shikimate pathway, thereby inhibiting aromatic amino acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases have a high tolerance to glyphosate.

Plant cells resistant to glyphosate toxicity can be produced by transforming plant cells to express glyphosate-resistant bacterial EPSP synthases. Notably, the bacterial gene from *Agrobacterium tumefaciens* strain CP4 has been used to confer herbicide resistance on plant cells following expression in plants. A mutated EPSP synthase from *Salmonella typhimurium* strain CT7 confers glyphosate resistance in bacterial cells, and confers glyphosate resistance on plant cells (U.S. Pat. Nos. 4,535,060; 4,769,061; and 5,094,945). However, there is a need for other herbicide resistance genes.

BRIEF SUMMARY OF THE INVENTION

Compositions and methods for conferring herbicide resistance to bacteria, plants, plant cells, tissues and seeds are provided. Compositions include nucleic acid molecules encoding sequences for herbicide resistance polypeptides, vectors comprising those nucleic acid molecules, and host cells comprising the vectors. Compositions comprising a coding sequence for a polypeptide that confers resistance or tolerance to glyphosate herbicides are provided, as well as antibodies to the polypeptides. Compositions of the present invention include synthetic nucleic acid molecules encoding herbicide resistance polypeptides. The coding sequences can be used in DNA constructs or expression cassettes for transformation and expression in organisms, including microorganisms and plants. Compositions also comprise transformed bacteria, plants, plant cells, tissues, and seeds. In addition, methods are provided for producing the polypeptides encoded by the synthetic nucleotides of the invention.

In particular, isolated nucleic acid molecules corresponding to herbicide resistance-conferring nucleic acid sequences are provided. Additionally, amino acid sequences corresponding to the polynucleotides are encompassed. In particular, the present invention provides for isolated nucleic acid molecules comprising the nucleotide sequence set forth in SEQ ID NO:1 or 2, a nucleotide sequence encoding the amino acid sequence shown in SEQ ID NO:3, the herbicide resistance nucleotide sequence deposited in a bacterial host as Accession No. B-30804, as well as variants and fragments thereof. Nucleotide sequences that are complementary to a nucleotide sequence of the invention, or that hybridize to a sequence of the invention are also encompassed.

BRIEF DESCRIPTION OF FIGURES

Figure 1:
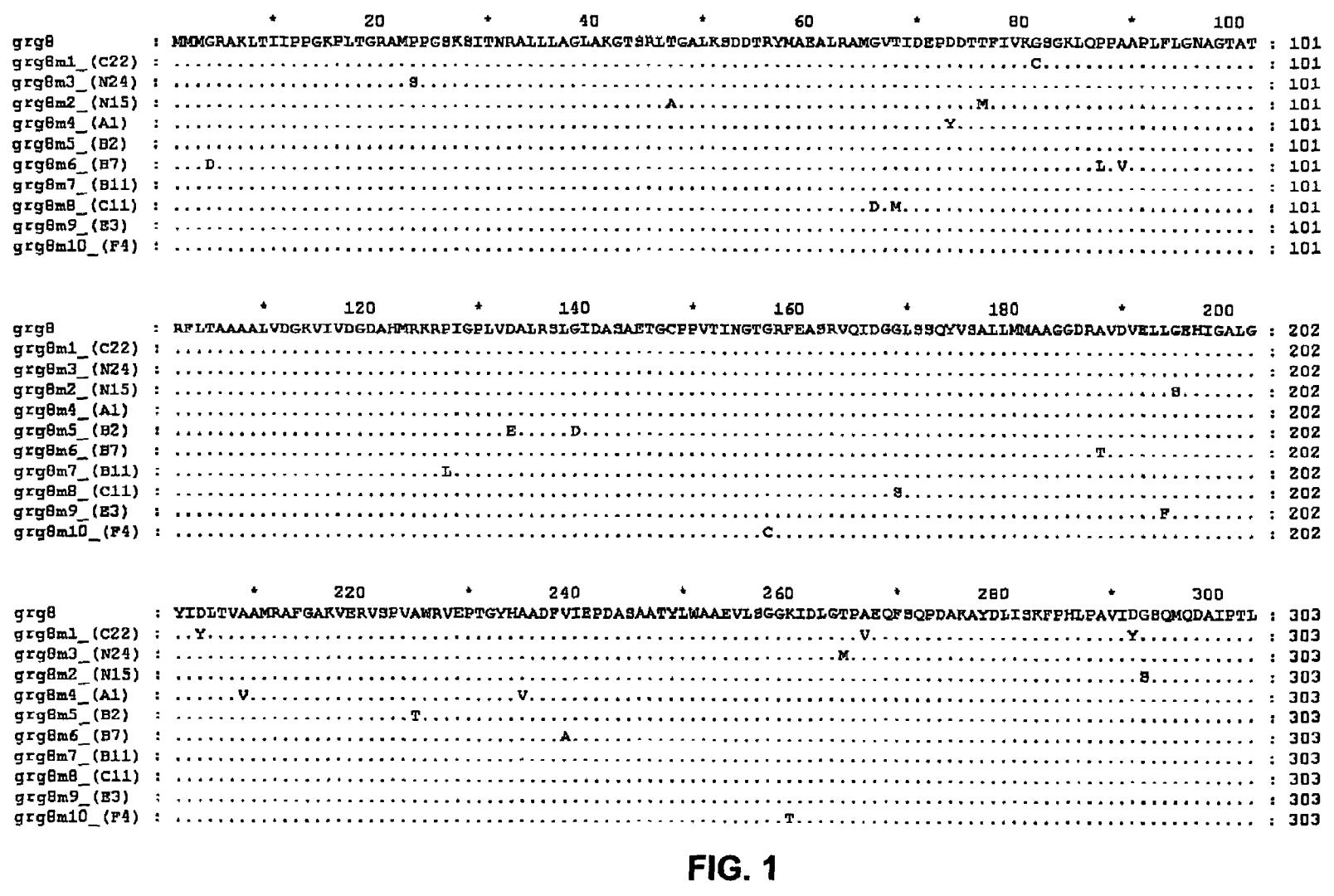

FIG. 1 shows an alignment of the amino acid sequences of GRG8 (SEQ ID NO:3), GRG8m1_(C22) (SEQ ID NO:5), GRG8m3_(N24) (SEQ ID NO:9), GRG8m2_(N15) (SEQ ID NO:7), GRG8m4_(A1) (SEQ ID NO:11), GRG8m5_(B2) (SEQ ID NO:13), GRG8m6_(B7) (SEQ ID NO:15), GRG8m7_(B11) (SEQ ID NO:17), GRG8m8_(C11) (SEQ ID NO:19), GRG8m9_(E3) (SEQ ID NO:21), and GRG8m10_(E4) (SEQ ID NO:23).

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is drawn to compositions and methods for regulating herbicide resistance in organisms, particularly in plants or plant cells. The methods involve transforming organisms with nucleotide sequences encoding the glyphosate resistance gene of the invention. The nucleotide sequences of the invention are useful for preparing plants that show increased tolerance to the herbicide glyphosate. Thus, transformed bacteria, plants, plant cells, plant tissues and seeds are provided. Compositions include nucleic acids and proteins relating to herbicide tolerance in microorganisms and plants as well as transformed bacteria, plants, plant tissues and seeds. Nucleotide sequences of the glyphosate resistance gene (grg8) and the amino acid sequences of the proteins encoded thereby are disclosed. The sequences find use in the construction of expression vectors for subsequent transformation into plants of interest, as probes for the isolation of other glyphosate resistance genes, as selectable markers, and the like.

Plasmids containing the herbicide resistance nucleotide sequences of the invention were deposited in the permanent collection of the Agricultural Research Service Culture Collection, Northern Regional Research Laboratory (NRRL) on Dec. 21, 2004, and assigned Accession No. NRRL B-30804. This deposit will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. § 1.808, sample(s) of the deposit with the ATCC. This deposit was made merely as a convenience for those of skill in the art and is not an admission that a deposit is required under 35 U.S.C. §112.

By "glyphosate" is intended any herbicidal form of N-phosphonomethylglycine (including any salt thereof) and other forms that result in the production of the glyphosate anion in planta. An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer time than cells that do not express the protein. A "glyphosate resistance protein" includes a protein that confers upon a cell the ability to tolerate a higher concentration of glyphosate than cells that do not express the protein, or to tolerate a certain concentration of glyphosate for a longer period of time than cells that do not express the protein. By "tolerate" or "tolerance" is intended either to survive, or to carry out essential cellular functions such as protein synthesis and respiration in a manner that is not readily discernable from untreated cells.

Isolated Nucleic Acid Molecules, and Variants and Fragments Thereof

One aspect of the invention pertains to isolated nucleic acid molecules comprising nucleotide sequences encoding herbicide resistance proteins and polypeptides or biologically active portions thereof, as well as nucleic acid molecules sufficient for use as hybridization probes to identify herbicide resistance-encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded.

Nucleotide sequences encoding the proteins of the present invention include the sequences set forth in SEQ ID NOS: 1 and 2, the herbicide resistance nucleotide sequence deposited in a bacterial host as Accession No. NRRL B-30804, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the herbicide resistance protein encoded by these nucleotide sequences is set forth in SEQ ID NO:3. The invention also encompasses nucleic acid molecules comprising nucleotide sequences encoding partial-length herbicide resistance proteins, and complements thereof.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated glyphosate resistance-encoding nucleic acid molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. An herbicide resistance protein that is substantially free of cellular material includes preparations of protein having less than about 30%, 20%, 10%, or 5% (by dry weight) of non-herbicide resistance protein (also referred to herein as a "contaminating protein").

Nucleic acid molecules that are fragments of these herbicide resistance-encoding nucleotide sequences are also encompassed by the present invention. By "fragment" is intended a portion of the nucleotide sequence encoding an herbicide resistance protein. A fragment of a nucleotide sequence may encode a biologically active portion of an herbicide resistance protein, or it may be a fragment that can be used as a hybridization probe or PCR primer using methods disclosed below. Nucleic acid molecules that are fragments of an herbicide resistance nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 contiguous nucleotides, or up to the number of nucleotides present in a full-length herbicide resistance-encoding nucleotide sequence disclosed herein (for example, 2000 nucleotides for SEQ ID NO:1, and 1257 nucleotides for SEQ ID NO:2). By "contiguous" nucleotides is intended nucleotide residues that are immediately adjacent to one another.

Fragments of the nucleotide sequences of the present invention generally will encode protein fragments that retain the biological activity of the full-length glyphosate resistance protein; i.e., herbicide-resistance activity. By "retains herbicide resistance activity" is intended that the fragment will have at least about 30%, at least about 50%, at least about 70%, or at least about 80% of the herbicide resistance activity of the full-length glyphosate resistance proteins disclosed herein as SEQ ID NO:3. Methods for measuring herbicide resistance activity are well known in the art. See, for example, U.S. Pat. Nos. 4,535,060, and 5,188,642, each of which are herein incorporated by reference in their entirety.

A fragment of an herbicide resistance-encoding nucleotide sequence that encodes a biologically active portion of a protein of the invention will encode at least about 15, 25, 30, 50, 75, 100, 125, 150, 175, 200, 250, 300, 350, 400 contiguous amino acids, or up to the total number of amino acids present in a full-length herbicide resistance protein of the invention (for example, 419 amino acids for the protein of the invention).

Herbicide resistance proteins of the present invention are encoded by a nucleotide sequence sufficiently identical to the nucleotide sequence of SEQ ID NO:1 or 2. The term "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403-410. BLAST nucleotide searches can be performed with the BLASTN program, score=100, wordlength=12, to obtain nucleotide sequences homologous to GDC-like nucleic acid molecules of the invention. BLAST protein searches can be performed with the BLASTX program, score=50, wordlength=3, to obtain amino acid sequences homologous to herbicide resistance protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al.(1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GeneDoc™. Genedoc™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., San Diego, Calif.). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the herbicide resistance-encoding nucleotide sequences include those sequences that encode the herbicide resistance protein disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the herbicide resistance proteins disclosed in the present invention as discussed below. Variant proteins encompassed by the present invention are biologically active, that is they retain the desired biological activity of the native protein, that is, herbicide resistance activity. By "retains herbicide resistance activity" is intended that the variant will have at least about 30%, at least about 50%, at least about 70%, or at least about 80% of the herbicide resistance activity of the native protein. Methods for measuring herbicide resistance activity are well known in the art. See, for example, U.S. Pat. Nos. 4,535,060, and 5,188,642, each of which are herein incorporated by reference in their entirety.

The skilled artisan will further appreciate that changes can be introduced by mutation into the nucleotide sequences of the invention thereby leading to changes in the amino acid sequence of the encoded herbicide resistance proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of an herbicide resistance protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in non-conserved regions that retain function. In general, such substitutions would not be made for conserved amino acid residues, or for amino acid residues residing within a conserved motif, where such residues are essential for protein activity. However, one of skill in the art would understand that functional variants may have minor conserved or non-conserved alterations in the conserved residues.

Alternatively, variant nucleotide sequences can be made by introducing mutations randomly along all or part of the coding sequence, such as by saturation mutagenesis, and the resultant mutants can be screened for the ability to confer herbicide resistance activity to identify mutants that retain activity. Following mutagenesis, the encoded protein can be expressed in a cell, and the activity of the protein can be determined using standard assay techniques.

Using methods such as PCR, hybridization, and the like corresponding herbicide resistance sequences can be identified, such sequences having substantial identity to the sequences of the invention. See, for example, Sambrook and Russell (2001) *Molecular Cloning: A Laboratory Manual* (Cold Spring Harbor Laboratory Press, Cold Spring Harbor, N.Y.) and Innis, et al. (1990) *PCR Protocols: A Guide to Methods and Applications* (Academic Press, St. Louis, Mo.).

In a hybridization method, all or part of the herbicide resistance nucleotide sequence can be used to screen cDNA or genomic libraries. Methods for construction of such cDNA and genomic libraries are generally known in the art and are disclosed in Sambrook and Russell (2001) supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known herbicide resistance-encoding nucleotide sequence(s) disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, 200, 250, 300, 350, 400, 500, 600, 700, 800, 900, 1000, 1200, 1400, 1600, or 1800 consecutive nucleotides of herbicide resistance-encoding nucleotide sequence(s) of the invention or a fragment or variant thereof. Methods for the preparation of probes for hybridization are generally known in the art and are disclosed in Sambrook and Russell (2001) supra, and Sambrook et al. (1989) *Molecular Cloning: A Laboratory Manual* (2d ed., Cold Spring Harbor Laboratory Press, Cold Spring Harbor, N.Y.), both of which are herein incorporated by reference.

For example, an entire herbicide resistance sequence disclosed herein, or one or more portions thereof, may be used as a probe capable of specifically hybridizing to corresponding herbicide resistance sequences and messenger RNAs. To achieve specific hybridization under a variety of conditions, such probes include sequences that are unique and are at least about 10 nucleotides in length, and at least about 20 nucleotides in length. Such probes may be used to amplify corresponding herbicide resistance sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, or less than about 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Herbicide resistance proteins are also encompassed within the present invention. By "herbicide resistance protein" is intended a protein having the amino acid sequence set forth in SEQ ID NO:3. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein as set forth in SEQ ID NO:3 and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity. Methods for measuring herbicide resistance activity are well known in the art. See, for example, U.S. Pat. Nos. 4,535,060, and 5,188,642, each of which are herein incorporated by reference in their entirety. As used here, a fragment comprises at least 8 contiguous amino acids of SEQ ID NO:3. The invention encompasses other fragments, however, such as any fragment in the protein greater than about 10, 20, 30, 50, 100, 150, 200, 250, 300, 350, or 400 amino acids.

By "variants" is intended proteins or polypeptides having an amino acid sequence that is at least about 60%, 65%, at least about 70%, 75%, at least about 80%, 85%, 90%, 91%, 92%, 93%, 94%, 95%, 96%, 97%, 98% or 99% identical to the amino acid sequence of SEQ ID NO:3. Variants also include polypeptides encoded by a nucleic acid molecule that hybridizes to the nucleic acid molecule of SEQ ID NOS:1 or 2, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining herbicide resistance activity. Methods for measuring herbicide resistance activity are well known in the art. See, for example, U.S. Pat. Nos. 4,535,060, and 5,188, 642, each of which are herein incorporated by reference in their entirety.

Bacterial genes, such as the grg8 gene of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants of grg8 that confer herbicide resistance. These herbicide resistance proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual* (Cold Spring Harbor Laboratory, Cold Spring Harbor, N.Y.); U.S. Pat. No. 4,196,265).

Altered or Improved Variants

It is recognized that the DNA sequence of grg8 may be altered by various methods, and that these alterations may result in DNA sequences encoding proteins with amino acid sequences different than that encoded by grg8. This protein may be altered in various ways including amino acid substitutions, deletions, truncations, and insertions. Methods for such manipulations are generally known in the art. For example, amino acid sequence variants of the GRG8 protein can be prepared by mutations in the DNA. This may also be accomplished by one of several forms of mutagenesis and/or by directed evolution. In some aspects, the changes encoded in the amino acid sequence will not substantially affect the function of the protein. Such variants will possess the desired herbicide resistance activity. However, it is understood that the ability of GRG8 to confer herbicide resistance may be improved by use of such techniques upon the compositions of the present invention. For example, GRG8 may be expressed in host cells that exhibit high rates of base misincorporation during DNA replication, such as XL-1 Red (Stratagene, La Jolla, Calif.). After propagation in such strains, grg8 DNA can be isolated (for example by preparing plasmid DNA, or by amplifying by PCR and cloning the resulting PCR fragment into a vector) and cultured in non-mutagenic strains. Clones containing mutations in grg8 can be identified by measuring improved resistance to an herbicide such as glyphosate, for example by growing cells in increasing concentrations of glyphosate and testing for clones that confer tolerance to increasing concentrations of glyphosate.

Alternatively, alterations may be made to the protein sequence of many proteins at the amino or carboxy terminus without substantially affecting activity. These alterations can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest; (2) introduce a binding domain, enzymatic activity, or epitope to facilitate either protein purification, protein detection, or other experimental uses known in the art; or, (3) target secretion or translation of a protein to a subcellular organelle, such as the periplasmic space of gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different herbicide resistance protein coding regions can be used to create a new herbicide resistance protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the herbicide resistance gene of the invention and other known herbicide resistance genes to obtain a new gene coding for a protein with an improved property of interest, such as an increased glyphosate resistance activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Transformation of Bacterial or Plant Cells

Provided herein are novel isolated genes that confer resistance to an herbicide. Also provided is an amino acid sequence of the GRG8 protein. The protein resulting from translation of this gene allows cells to function in the presence of concentrations of an herbicide that are otherwise toxic to cells including plant cells and bacterial cells. In one aspect of the invention, the grg8 gene is useful as a marker to assess transformation of bacterial or plant cells.

By engineering grg8 to be (1) expressed from a bacterial promoter known to stimulate transcription in the organism to be tested, (2) properly translated to generate an intact GRG8 peptide, and (3) placing the cells in an otherwise toxic concentration of herbicide, cells that have been transformed with DNA by virtue of their resistance to herbicide can be identified. By "promoter" is intended a nucleic acid sequence that functions to direct transcription of a downstream coding sequence. The promoter, together with other transcriptional and translational regulatory nucleic acid sequences, (also termed "control sequences") are necessary for the expression of a DNA sequence of interest.

Transformation of bacterial cells is accomplished by one of several techniques known in the art, including but not limited to, electroporation or chemical transformation (See, for example, Ausubel (ed.) (1994) *Current Protocols in Molecular Biology* (John Wiley and Sons, Inc., Indianapolis, Ind.)). Markers conferring resistance to toxic substances are useful in identifying transformed cells (having taken up and expressed the test DNA) from non-transformed cells (those not containing or not expressing the test DNA). In one aspect of the invention, the grg8 gene is useful as a marker to assess transformation of bacterial or plant cells.

Transformation of plant cells can be accomplished in a similar fashion. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants, cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The grg8 gene of the invention may be modified to obtain or enhance expression in plant cells. The herbicide resistance sequences of the invention may be provided in expression cassettes for expression in the plant of interest. "Plant expression cassette" includes DNA constructs that are capable of resulting in the expression of a protein from an open reading frame in a plant cell. The cassette will include in the 5'-3' direction of transcription, a transcriptional initiation region (i.e., promoter) operably-linked to a DNA sequence of the invention, and a translational and transcriptional termination region (i.e., termination region) functional in plants. The cassette may additionally contain at least one additional gene to be co-transformed into the organism, such as a selectable marker gene. Alternatively, the additional gene(s) can be provided on multiple expression cassettes. Such an expression cassette is provided with a plurality of restriction sites for insertion of the herbicide resistance sequence to be under the transcriptional regulation of the regulatory regions.

The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. "Heterologous" generally refers to the nucleic acid sequences that are not endogenous to the cell or part of the native genome in which they are present, and have been added to the cell by infection, transfection, microinjection, electroporation, microprojection, or the like. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Often, such constructs will also contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this transport typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. The plant expression cassette can also be engineered to contain an intron, such that mRNA processing of the intron is required for expression.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence. Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region, may be native with the herbicide resistance sequence of the present invention, or may be derived from another source. Convenient termination regions are available from the Ti-plasmid of *A. tumefaciens,* such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing host-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium,* and transfer of DNA by cleavage at border sequences and vir-mediated DNA transfer, as in understood in the art (Hellens and Mullineaux (2000) *Trends in Plant Science,* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plants and produce fertile seeds (e.g. Hiei et al. (1994) *The Plant Journal* 6:271-282;

Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Plants

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of the heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual* (Cold Spring Harbor Laboratory Press, Cold Spring Harbor, N.Y.)). PCR is carried out using oligonucleotide primers specific to the gene of interest or *Agrobacterium* vector background, etc.

Plant transformation may be confirmed by Southern blot analysis of genomic DNA (Sambrook and Russell (2001) supra). In general, total DNA is extracted from the transformant, digested with appropriate restriction enzymes, fractionated in an agarose gel and transferred to a nitrocellulose or nylon membrane. The membrane or "blot" can then be probed with, for example, radiolabeled $^{32}$P target DNA fragment to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, and blotted onto a nylon filter according to standard procedures that are routinely used in the art (Sambrook and Russell (2001) supra). Expression of RNA encoded by the grg8 is then tested by hybridizing the filter to a radioactive probe derived from a GDC by methods known in the art (Sambrook and Russell (2001) supra)

Western blot and biochemical assays and the like may be carried out on the transgenic plants to determine the presence of protein encoded by the herbicide resistance gene by standard procedures (Sambrook and Russell (2001) supra) using antibodies that bind to one or more epitopes present on the herbicide resistance protein.

The following examples are offered by way of illustration and not by way of limitation.

EXPERIMENTAL

Example 1

Isolation of ATX4145

ATX4145 was isolated by plating samples of soil on Enriched Minimal Media (EMM) containing glyphosate as the sole source of phosphorus. Since EMM contains no aromatic amino acids, a strain must be resistant to glyphosate in order to grow on this media.

Two grams of soil were suspended in approximately 30 ml of water, and sonicated for 30 seconds in a sonicating water bath. The sample was vortexed for 5 seconds and permitted to settle for 60 seconds. This process was repeated 3 times. 100 μl of this suspension was added to 3 ml of EMM supplemented with 4 mM glyphosate (pH 6.0). EMM contains (per 900 mls): 10 g sucrose, 2 g $NaNO_3$, 1.0 ml 0.8 M $MgSO_4$, 1.0 ml 0.1 M $CaCl_2$, 1.0 ml Trace Elements Solution (In 100 ml of 1000× solution: 0.1 g $FeSO_4.7H_2O$, 0.5 mg $CuSO_4.5H_2O$, 1.0 mg $H_3BO_3$, 1.0 mg $MnSO_4.5H_2O$, 7.0 mg $ZnSO_4.7H_2O$, 1.0 mg $MoO_3$, 4.0 g KCl). The culture was shaken on a tissue culture roller drum for sixteen days at 21° C. and then 100 μl was used to inoculate 3 ml of fresh EMM containing 4 mM glyphosate as the only phosphorus source. After five days, 100 μl was used to inoculate another fresh 3 ml culture. After sufficient growth, the culture was plated onto solid media by streaking a 1 μl loop onto the surface of agar plate containing EMM agar containing 5 mM glyphosate as the sole phosphorus source and stored at 21° C. The culture was then replated for isolation. One particular strain, designated ATX4145, was selected due to its ability to grow in the presence of high glyphosate concentrations. On Luria Bertani (LB) agar, colonies are white, circular, pinsize to 1 mm and stain Gram negative.

Example 2

Preparation and Screening of Cosmid Libraries

Total DNA was extracted from a culture of ATX4145 using methods commonly known in the art. The DNA was partially digested with restriction enzyme Sau3A1 and ligated with SuperCos (Stratagene) vector fragment according to the manufacturer's directions. Ligation products were packaged into phage particles using GigaPack III XL packaging extract (Stratagene), transfected into *E. coli* cells, and plated on LB Agar containing 50 μg/ml kanamycin to select for colonies containing cosmids. Approximately 1100 colonies were picked for screening.

Colonies were grown in rich liquid medium containing 50 μg/ml kanamycin, then pinned onto M63 agar medium containing 50 μg/ml kanamycin and 7 mM glyphosate. M63 agar medium contains 100 mM $KH_2PO_4$, 15 mM $(NH_4)_2SO_4$, 50 μM $CaCl_2$, 1 μM $FeSO_4$, 50 μM $MgCl_2$, 55 mM glucose, 25 mg/liter L-proline, 10 mg/liter thiamine HCl, sufficient NaOH to adjust the pH to 7.0, and 15 g/liter agar. Several colonies which grew in the presence of 7 mM glyphosate were identified. Cosmid DNA was prepared from each of these colonies and re-transformed into *E. coli* XL1 Blue MRF cells. In each case cells retransformed with cosmid DNA grew on M63 medium in the presence of 5 mM glyphosate while cells containing empty SuperCos vector did not. One cosmid, designated 3-M5, was selected for further characterization. This cosmid was later renamed pAX298.

Example 3

Identification of grg8 in Cosmid pAX298

To identify the gene(s) responsible for the glyphosate-resistance shown by cosmid pAX298, DNA from this clone was mutagenized with transposable elements. In this method, one identifies clones that have suffered transposon insertions, and have lost the ability to confer glyphosate resistance. The location of the transposon insertions identifies the open reading frame responsible for the glyphosate resistance phenotype.

Cosmid pAX298 was subjected to in vitro transposon mutagenesis using an EZ::TN Insertion Kit (Epicentre, Madison, Wis.) and the manufacturer's protocol. This process randomly inserts a transposon fragment into the cosmid DNA and thus randomly disrupts the function of genes in the cosmid. This particular transposon contains a gene encoding resistance to trimethoprim, so transposon insertion clones may be selected by the ability to grow in the presence of that antibiotic. The locations of the transposon insertions may be determined by restriction fragment mapping or by sequencing with primers which anneal in the transposon. Transposon insertion clones of pAX298 were plated on M63 medium containing glyphosate. Three clones were found which had lost the ability to grow in the presence of glyphosate, indicating that the transposon had disrupted the gene responsible for resistance.

The DNA sequence was determined for the region of pAX298 containing the transposon insertions using sequencing methods well known in the art and is presented below. An open reading frame (ORF, bases 296 through 1555 of SEQ ID NO:1) was identified. Analysis of sequence data from four transposon insertion picks that had lost resistance to glyphosate revealed that all four insertions were within the ORF. This indicates that the ORF encodes the resistance conferred by the cosmid.

Example 4

Homology of GRG8 with Other Proteins

The deduced amino acid sequence of this ORF has homology to EPSP synthase enzymes, indicating that the ORF encodes an EPSP synthase. Cosmid pAX298 was transformed into *E. coli* aroA-, a strain in which the native aroA gene, encoding EPSP synthase, has been deleted. This strain cannot grow on M63 medium because it requires exogenously supplied aromatic amino acids. The presence of cosmid pAX298 complemented the aroA-phenotype, that is, it allowed the strain to grow on M63 medium without exogenously supplied aromatic amino acids. This is further evidence that the cosmid contains an EPSP synthase gene. This gene was named grg8.

Examination of the deduced amino acid sequence (SEQ ID NO:3) revealed that it does not contain the four domains typical of Class II EPSP synthase enzymes. Thus it is a novel, non-Class II, glyphosate-resistant EPSP synthase.

Example 5

Engineering of grg8 for Expression of GRG8 Protein in *E. coli*

The grg8 open reading frame (ORF) was amplified by PCR, cloned into the plasmid vector pCR-Blunt-II from Invitrogen, and transformed into *E. coli* strain DH5α. Plasmid DNA was prepared and the presence and orientation of the inserts were determined by restriction digest. One clone contained the ORF in the forward orientation with respect to the lac promoter in the vector. This plasmid was named pAX299. The insert was sequenced and the plasmid was tested for the ability to confer resistance to glyphosate.

Plasmid pAX299 containing the grg8 ORF was deposited at the Agricultural Research Service Culture Collection (NRRL) on Dec. 21, 2004, and assigned Accession No. NRRL B-30804.

Example 6 grg8 Confers Resistance to High Levels of Glyphosate pAX299 was tested for the ability to grow on M63 medium in the presence of glyphosate using cells containing empty vector as a control. The plasmid pAX296 in host strain DH5α was used as a negative control. This plasmid contains a fragment of tobacco genomic DNA cloned into the vector pCR-Blunt-II. The results are summarized in Table 1. Starter cultures of the two strains were grown in M63 broth with 50 µg/ml kanamycin to maintain the plasmid. The starter cultures were diluted to approximately equal cell densities, as determined by measuring OD600, then diluted 1 to 200 into 3 ml of M63 broth containing 0 to 200 mM glyphosate. Triplicate 3 ml cultures of each strain in each concentration were grown. Cultures were grown at 37° C. with constant shaking. After about 46 hours, 0.3 ml aliquots were withdrawn and the $OD_{600}$ was measured. The results are presented in Table 1. Values represent means + standard deviations. These results demonstrate that GRG8 confers resistance to high levels of glyphosate.

TABLE 1

Glyphosate resistance of pAX299 containing grg8

| Glyphosate concentration (mM) | grg8 | Negative control |
|---|---|---|
| 0 | 1.18 ± 0.029 | 1.09 ± 0.024 |
| 10 | 1.15 ± 0.018 | 0.04 ± 0.0008 |
| 20 | 1.10 ± 0.043 | 0.04 ± 0.0004 |
| 50 | 1.20 ± 0.037 | 0.04 ± 0.0004 |
| 100 | 1.31 ± 0.024 | 0.04 ± 0.0005 |
| 200 | 0.05 ± 0.004 | 0.04 ± 0.0004 |

Example 7

Purification of GRG8 Expressed as a 6× His-tagged Protein in E. coli

The grg8 coding region was amplified by PCR using PfuUltra™ DNA polymerase (Stratagene). Oligonucleotides used to prime PCR are designed to introduce restriction enzyme recognition sites near the 5' and 3' ends of the resulting PCR product. The resulting PCR product is digested with Sal I. The digested product is cloned into the 6× His-tag expression vector pRSF1b (Novagen), prepared by digestion with Sal I. The resulting clone contains GRG8 in the same translational reading frame as, and immediately C-terminal to, the 6× His tag. General strategies for generating such clones, and for expressing proteins containing 6× His-tag are well known in the art.

The ability of this clone to confer glyphosate resistance is confirmed by plating cells onto M63 media containing 5 mM glyphosate. The ability the clone containing grg8 to grow at this concentration of glyphosate is determined. The level of expression of GRG8 protein may be determined on an SDS-PAGE protein gel. GRG8 protein can be isolated by purification of the induced GRG8 protein by chromatography on, for example, Ni-NTA Superflow Resin (Qiagen), as per manufacturer's instructions.

Example 8

Mutagenesis of grg8 and Isolation of Functional Variants

The grg8 open reading frame was mutagenized using PCR-based mutagenesis as known in the art. Plasmid pAX700, containing grg8, was amplified using the Genemorph® mutagenesis kit (Stratagene) using varying amounts of input DNA. The resulting PCR products were purified and digested with Bam HI and Hind III, repurified, and ligated into a modified pRSF1b vector (Novagen). The resulting libraries were transformed into E. coli, picked into 384 well plates, and grown to saturation at 37° C. The resulting 384 stock plates were stamped onto minimal media (M63 plus) supplemented with kanamycin, and with varying concentrations of glyphosate. Mutagenized clones that conferred resistance to 50 mM glyphosate (shown in Table 2) were selected. For a subset of these clones, DNA was prepared, and the DNA sequence of the grg8 variant was determined.

TABLE 2

Growth of E. coli expressing grg8 variants in the presence of glyphosate

| Mutation | Original Name | Growth on 50 mM glyphosate |
|---|---|---|
| Vector control | — | − |
| grg8 | grg8 | +++ |
| grg8m1 | C22 | +++ |
| grg8m2 | N15 | + |
| grg8m3 | N24 | +++ |
| grg8m4 | A1 | +++ |
| grg8m5 | B2 | +++ |
| grg8m6 | B7 | +++ |
| grg8m7 | B11 | +++ |
| grg8m8 | C11 | +++ |
| grg8m9 | E3 | +++ |
| grg8m10 | F4 | +++ |

Example 9

Engineering grg8 for Plant Transformation

The grg8 open reading frame (ORF) is amplified by polymerase chain reactions from a full-length cDNA template. HindIII restriction sites are added to each end of the ORF during PCR. Additionally, the nucleotide sequence ACC is added immediately 5' to the start codon of the gene to increase translational efficiency (Kozak (1987) 15:8125-8148; Joshi (1987) *Nucleic Acids Research* 15:6643-6653). The PCR product is cloned and sequenced, using techniques well known in the art, to ensure that no mutations are introduced during PCR.

The plasmid containing the grg8 PCR product is digested with, for example, Hind III, and the fragment containing the intact ORF is isolated. In this example, the fragment is cloned into the Hind III site of a plasmid such as pAX200, a plant expression vector containing the rice actin promoter (McElroy et al. (1991) *Molec. Gen. Genet.* 231:150-160) and the PinII terminator (An et al. (1989) *The Plant Cell* 1:115-122). The promoter—gene—terminator fragment from this intermediate plasmid is then subcloned into a plasmid such as pSB11 (Japan Tobacco, Inc.) to form a final plasmid, referred to herein as pSB11GRG8. pSB11GRG8 is organized such that the DNA fragment containing the promoter—grg8—terminator construct may be excised by double digestion with appropriate restriction enzymes and also used for transformation into plants by, for example, aerosol beam injection. The structure of pSB11GRG8 is verified by restriction digests and gel electrophoresis and by sequencing across the various cloning junctions.

The plasmid is mobilized into *Agrobacterium tumefaciens* strain LBA4404 which also harbors the plasmid pSB1 (Japan Tobacco, Inc.), using triparental mating procedures well known in the art, and plating on media containing spectinomycin. Plasmid pSB11GRG8 carries antibiotic resistance but is a narrow host range plasmid and cannot replicate in *Agrobacterium*. Antibiotic-resistant colonies arise when pSB11GRG8 integrates into the broad host range plasmid, such as pSB1, through homologous recombination. The resulting cointegrate product is verified by Southern hybridization. The *Agrobacterium* strain harboring the cointegrate can then be used to transform maize, for example by the PureIntro method (Japan Tobacco).

Example 10

Transformation of grg8 into Plant Cells

Maize ears are best collected 8-12 days after pollination. Embryos are isolated from the ears, and embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express GRG8 in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| Components | per liter | Source |
|---|---|---|
| DN62A5S Media | | |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

Example 11

Transformation of grg8 into Maize Plant Cells by *Agrobacterium*-Mediated Transformation Ears are best collected 8-12 days after pollination. Embryos are isolated from the ears, and embryos 0.8-1.5 mm in size are preferred to be used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule encoding a 5-enolpyruvylshikimate-3-phosphate (EPSP) synthase enzyme selected from the group consisting of:
   a) a nucleic acid molecule comprising the nucleotide sequence of SEQ ID NO:1 or 2, or a complement thereof;
   b) the herbicide resistance nucleotide sequence of the DNA insert of the plasmid deposited as Accession No. NRRL B-30804, or a complement thereof;
   c) a nucleic acid molecule which encodes a polypeptide comprising the amino acid sequence of SEQ ID NO:3; and
   d) a nucleic acid molecule comprising a nucleotide sequence encoding a polypeptide having at least 95% amino acid sequence identity to the amino acid sequence of SEQ ID NO:3, wherein said polypeptide has herbicide resistance activity.

2. The isolated nucleic acid molecule of claim 1, wherein said nucleotide sequence is a synthetic sequence that has been designed for expression in a plant.

3. A vector comprising the nucleic acid molecule of claim 1.

4. The vector of claim 3, further comprising a nucleic acid molecule encoding a heterologous polypeptide.

5. A host cell that contains the vector of claim 3.

6. The host cell of claim 5 that is a bacterial host cell.

7. The host cell of claim 5 that is a plant cell.

8. A transgenic plant comprising the host cell of claim 7.

9. The plant of claim 8, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

10. A transformed seed of the plant of claim 8.

11. The isolated nucleic acid of claim 1, wherein said nucleic acid further encodes one or more of the following:
   a) an aspartic acid substituted for a glycine at amino acid 4 of SEQ ID NO:3;
   b) a seine substituted for a proline at amino acid 12 of SEQ ID NO:3;
   c) an alanine substituted for the threonine residue at amino acid 47 of SEQ ID NO:3;
   d) an aspartic acid substituted for a glycine at amino acid 66 of SEQ ID NO:3;
   e) a methionine substituted for a threonine at amino acid 68 of SEQ ID NO:3;
   f) a tyrosine substituted for the aspartic acid residue at amino acid 73 of SEQ ID NO:3;
   g) a methionine substituted for the threonine residue at amino acid 76 of SEQ ID NO:3;
   h) a cysteine substituted for the glycine residue at amino acid 81 of SEQ ID NO:3;
   i) a leucine substituted for the proline residue at amino acid 87 of SEQ ID NO:3;
   j) a valine substituted for the alanine residue at amino acid 89 of SEQ ID NO:3;
   k) a leucine substituted for the proline residue at amino acid 127 of SEQ ID NO:3;
   l) a glutamic acid substituted for an aspartic acid residue at amino acid 133 of SEQ ID NO:3;
   m) an aspartic acid substituted for a glycine residue at amino acid 139 of SEQ ID NO:3;
   n) a cysteine substituted for a glycine residue to amino acid 157 of SEQ ID NO:3;
   o) a serine substituted for a glycine residue at amino acid 169 of SEQ ID NO:3;
   p) a threonine substituted for an alanine residue at amino acid 188 of SEQ ID NO:3;
   q) a phenylalanine substituted for a leucine residue at amino acid 194 of SEQ ID NO:3;
   r) a serine substituted for a glycine residue at amino acid 195 of SEQ ID NO:3;
   s) a tyrosine substituted for an aspartic acid residue at amino acid 205 of SEQ ID NO:3;
   t) a valine substituted for an alanine residue at amino acid 209 of SEQ ID NO:3;
   u) a threonine substituted for an alanine residue at amino acid 225 of SEQ ID NO:3;
   v) a valine substituted for an alanine residue at amino acid 235 of SEQ ID NO:3;
   w) an alanine substituted for a valine residue at amino acid 239 of SEQ ID NO:3;
   x) a threonine substituted for a lysine residue at amino acid 260 of SEQ ID NO:3;
   y) a methionine substituted for a threonine residue at amino acid 265 of SEQ ID NO:3;
   z) a tyrosine substituted for an aspartic acid residue at amino acid 292 of SEQ ID NO:3;
   aa) a serine substituted for a glycine residue at amino acid 293 of SEQ ID NO:3;
   bb) an alanine substituted for a valine residue at amino acid 317 of SEQ ID NO:3;
   cc) an asparagine substituted for a serine residue at amino acid 335 of SEQ ID NO:3;
   dd) a serine substituted for an alanine residue at amino acid 355 of SEQ ID NO:3;
   ee) an asparagine substituted for an isoleucine residue at amino acid 364 of SEQ ID NO:3; or ff) a valine substituted for an alanine residue at amino acid 382 of SEQ ID NO:3.

12. A method for conferring resistance to an herbicide in a plant, said method comprising transforming said plant with a DNA construct, said construct comprising a promoter that drives expression in a plant cell operably linked with the nucleotide sequence of claim 1, and regenerating a transformed plant.

13. The method of claim 12, wherein said herbicide is a glyphosate.

14. A plant having stably incorporated into its genome a DNA construct comprising a nucleotide sequence that encodes a 5-enolpyruvylshikimate-3-phosphate (EPSP) synthase protein having herbicide resistance activity, wherein said nucleotide sequence is selected from the group consisting of:

a) a nucleotide sequence of SEQ ID NO:1 or 2;
b) a nucleotide sequence encoding a polypeptide comprising an amino acid sequence of SEQ ID NO:3;
c) a nucleotide sequence encoding a polypeptide having at least 95% amino acid sequence identity to the amino acid sequence of SEQ ID NO:3, wherein said polypeptide has herbicide resistance activity; and
d) the herbicide resistance nucleotide sequence of the DNA insert of the plasmid deposited as Accession No. NRRL B-30804;

wherein said nucleotide sequence is operably linked to a promoter that drives expression of a coding sequence in a plant cell.

15. The plant of claim 14, wherein said plant is a plant cell.

\* \* \* \* \*

UNITED STATES PATENT AND TRADEMARK OFFICE
CERTIFICATE OF CORRECTION

| | | |
|---|---|---|
| PATENT NO. | : 7,534,937 B2 | |
| APPLICATION NO. | : 11/315678 | |
| DATED | : May 19, 2009 | |
| INVENTOR(S) | : Hammer et al. | |

It is certified that error appears in the above-identified patent and that said Letters Patent is hereby corrected as shown below:

<u>Column 85,</u>

Line 56, "seine" should read --serine--.

Signed and Sealed this

Eleventh Day of August, 2009

David J. Kappos
*Director of the United States Patent and Trademark Office*